(12) United States Patent
Stashenko et al.

(10) Patent No.: US 6,403,304 B1
(45) Date of Patent: Jun. 11, 2002

(54) HUMAN OSTEOCLAST-SPECIFIC AND -RELATED DNA SEQUENCES

(75) Inventors: Philip Stashenko, Norfolk; Yi-Ping Li, Boston; Anne L. Wucherpfennig, Brookline, all of MA (US)

(73) Assignee: Forsyth Dental Infirmary for Children, Boston, MA (US)

( * ) Notice: Subject to any disclaimer, the term of this patent is extended or adjusted under 35 U.S.C. 154(b) by 0 days.

(21) Appl. No.: 08/684,932

(22) Filed: Jul. 19, 1996

Related U.S. Application Data

(63) Continuation-in-part of application No. 08/392,678, filed on Feb. 23, 1995, now Pat. No. 5,552,281, which is a continuation of application No. 08/045,270, filed on Apr. 6, 1993, now abandoned, and a continuation of application No. 08/605,378, filed on Feb. 22, 1996, now abandoned.
(60) Provisional application No. 60/001,292, filed on Jul. 20, 1995.

(51) Int. Cl.$^7$ .......................... C07H 21/04; C12N 5/10; C12N 15/70; C12Q 1/68

(52) U.S. Cl. ................. 435/6; 435/252.3; 435/320.1; 435/69.1; 536/23.1

(58) Field of Search ................. 435/6, 252.3, 320.1, 435/69.1; 536/23.1

(56) References Cited

U.S. PATENT DOCUMENTS

| 5,501,969 A | * | 3/1996 | Hastings et al. | ......... 435/240.2 |
| 5,736,357 A | * | 4/1998 | Bromme et al. | ........... 435/69.1 |

FOREIGN PATENT DOCUMENTS

| WO | 94/23033 | 10/1994 |
| WO | 96/13523 | 5/1996 |

OTHER PUBLICATIONS

Search report regarding Seq. Id. 7, 18 and 24 re. Hastings et al. and Bromme et al., Feb. 2000.*
Blair, Harry C., et al., "Extracellular–matrix Degradation at Acid pH Avian Osteoclast Acid Collagenase Isolation and Characterization", *Biochemical Journal* 290(3):873–884 (1993).
Tezuka, Ken–Ichi, et al., "Identification of Osteopontin in Isolated Rabbit Osteoclasts", *Biochemical and Biophysical Research Communications* 186(2):911–917 (1992).
Davies, John, et al., "The Osteoclast Functional Antigen, Implicated in the Regulation of Bone Resorption, is Biochemically Related to the Vitronectin Receptor", *The Journal of Cell Biology* 109(4):1817–1826 (1989).
Tezuka, Ken–Ichi, et al., "Molecular Cloning of a Possible Cysteine Proteinase Predominantly Expressed in Osteoclasts", *Journal of Biological Chemistry* 269(2):1106–1109 (1994).

Maciewicz, R.A. and Etherington, D.J., "Comparison of Four Cathepsin (B, L, N and S) with Collagenolytic Activity From Rabbit Spleen", *Biochem. J.* 256:433–440 (1988).
Rifkin, B.R. et al., "Cathepsin B and L Activities in Isolated osteoclasts", *Biochem. Biophys. Res. Comm.* 179:63–69 (1991).
Goto, T. et al., "Immunohistochemical Localization of Cathepsins B, D and L in the Rat Osteoclast", *Histochemistry* 99:411–414 (1993).
Karhukorpi, E.K. et al., "A Difference in the Enzyme Contents of Resorption Lecunac and Secondary Lysosomes of Osteoclasts", *Acta. Histochemical* 92:1–11 (1992).
Sasaki, T., Ueno–Matsuda, E., "Cystein–proteinase Localization in Osteoclasts: An Immunocytochemical Study", *Cell Tissue Res.* 271:177–179 (1993).
Delaisse, J.M. et al., "Collagenolytic Cysteine Proteinases of Bone Tissue", *Biochem. J.* 279:167–174 (1991).
Page, A.E. et al., "Human Osteoclastomas Contain Multiple Forms of Cathepsin B", *Biochem. Biophys. Acta.* 1116:57–66 (1992).
Van Noorden, C.J.F., et al., "Selective Inhibition of Cysteine Proteinases by Z–Phe–AlaCH2F Suppresses Digestion of Collagen by Fibroblasts and Osteoclasts", *Biochem. Biophys. Res. Comm.* 178:178–184 (1991).
Van Noorden, C.J.F., et al., "Localization of Cathepsin B Activity in Fibroblasts and Chondrocytes by Continous Monitoring of the Formation of a Final Fluorescent Reaction Product Using 5–Nitrosalicylaldehyde", *Histochemical Journal* 19:483–487 (1987).
Horton, M.A. et al., "Monoclonal Antibodies to Osteoclastomas (Giant Cell Bone Tumors): Definition of Osteoclast–specific Cellular Antigens", *Cancer Research* 45:5663–5669 (1985).
Hayman, A.R. et al., "Purification and Characterization of a Tartrate–resistant Acid Phosphatase from Human Osteoclastomas", *Biochem. J.* 261:601–609 (1989).
Sandberg, M. et al., "Localization of the Expression of Types I, III, and IV Collagen, TGF–β1 and c–fos Genes in Developing Human Calvarial Bones", *Developmental Biology* 130:324–334 (1988).
Sandberg, M. et al., "Enhanced Expression of the TGF–β and c–fos mRNAs in the Growth Plates of Developing Human Long Bones", *Development* 102: 461–470 (1988).
Ek–Rylander, B. et al., "Cloning, Sequence, and Developmental Expression of a Type 5, Tartrate–Resistant, Acid Phosphatase of Rat Bone", *The J. of Biological Chem.* 266:24684–24689 (1991).

(List continued on next page.)

Primary Examiner—Bennett Celsa
(74) Attorney, Agent, or Firm—Hamilton, Brook, Smith & Reynolds, P.C.

(57) ABSTRACT

The present invention relates to purified osteoclast-specific or -related DNA sequences and a method for identifying such sequences. DNA constructs capable of replicating osteoclast-specific or -related DNA and DNA constructs capable of directing expression in a host cell of osteoclast-specific or -related DNA are also described.

5 Claims, 4 Drawing Sheets

OTHER PUBLICATIONS

Peng, et al., "Alternative mRNA Splicing Generates Tissue-specific Isoforms of 116–kDA Polypeptide of Vacuolar Proton Pump", *J. of Biol. Chem.* 269(25):17262–17266 (1994).

Crider, et al., "Bafilomycin Inhibits Proton Flow through the $H^+$ Channel of Vacuolar Proton Pumps", *J. of Biol. Chem.* 269:(26)17379–17381 (1994).

Perin, et al., "Structure of the 116–kDa Polypeptide of the Clathrin–coated Vesicle/Synaptic Vesicle Proton Pump", *J. of Biol. Chem.* 266(6):3877–3881 (1991).

Li, Y–P. et al., "Molecular Cloning and Characterization of a Putative Novel Human Osteoclast–Specific 116–kDa Vacuolar Proton Pump Subunit", *Biochemical and Biophysical Research Communications*, 218:813–821 (1996).

Shapiro, L.H. et al., "Carbonic Anhydrase II is Induced in HL–60 Cells by 1,25–Dihydroxyvitamin $D_3$: a Model for Osteoclast Gene Regulation", *FEBS Letters*, 249(2):307–310 (1989).

Ketcham, C.M. et al., "Molecular Cloning of the Type 5, Iron–Containing, Tartrate–Resistant Acid Phosphatase from Human Placenta", *The Journal of Biological Chemistry*, 264(1):557–563 (1989).

Wilhelm, S.M. et al., "SV40–Transformed Human Lung Fibroblasts Secrete a 92–kDa Type IV Collagenas, Which Is Identical to That Secreted by Normal Human Macrophages", *The Journal of Biological Chemistry*, 264(29):17213–17221 (1989).

* cited by examiner

```
1     AGACACCTCT GCCCTCACCA TGAGCCTCTG GCAGCCCCTG GTCCTGGTGC TCCTGGTGCT
61    GGGCTGCTGC TTTGCTGCCC CCAGACAGCG CCAGTCCACC CTTGTGCTCT TCCCTGGAGA
121   CCTGAGAACC AATCTCACCG ACAGGCAGCT GGCAGAGGAA TACCTGTACC GCTATGGTTA
181   CACTCGGGTG GCAGAGATGC GTGGAGAGTC GAAATCTCTG GGGCCTGCGC TGCTGCTTCT
241   CCAGAAGCAA CTGTCCCTGC CCGAGACCGG TGAGCTGGAT AGCGCCACGC TGAAGCCCAT
301   GCGAACCCCA CGGTGCGGGG TCCCAGACCT GGGCAGATTC CAAACCTTTG AGGGCGACCT
361   CAAGTGGCAC CACCACAACA TCACCTATTG GATCCAAAAC TACTCGGAAG ACTTGCCGCG
421   GGCGGTGATT GACGACGCCT TTGCCCGCGC CTTCGCACTG TGGAGCGCGG TGACGCCGCT
481   CACCTTCACT CGCGTGTACA GCCGGGACGC AGACATCGTC ATCCAGTTTG GTGTCGCGGA
541   GCACGGAGAC GGGTATCCCT TCGACGGGAA GGACGGGCTC CTGGCACACG CCTTTCCTCC
601   TGGCCCCGGC ATTCAGGAG ACGCCCATTT CGACGATGAC GAGTTGTGGT CCCTGGGCAA
661   GGGCGTCGTG GTTCCAACTC GGTTTGGAAA CGCAGATGGC GCGGCCTGCC ACTTCCCCTT
721   CATCTTCGAG GGCCGCTCCT ACTCTGCCTG CACCACCGAC GGTCGCTCCG ACGGGTTGCC
781   CTGGTCCAGT ACCACGGCCA ACTACGACAC CGACGACCGG TTTGGCTTCT GCCCCAGCGA
841   GAGACTCTAC ACCCGGGACG GCAATGCTGA TGGGAAACCC TGCCAGTTTC CATTCATCTT
901   CCAAGGCCAA TCCTACTCCG CCTGCACCAC GGACGGTCGC TCCGACGGCT ACCGCTGGTG
961   CGCCACCACC GCCAACTACG ACCGGACAA GCTCTTCGGC TTCTGCCCGA CCCGAGCTGA
1021  CTCGACGGTG ATGGGGGGCA ACTCGGCGGG GGAGCTGTGC GTCTTCCCCT TCACTTTCCT
1081  GGGTAAGGAG TACTCGACCT GTACCAGCGA GGGCCGCGGA GATGGGCGCC TCTGGTGCGC
1141  TACCACCTCG AACTTTGACA GCGACAAGAA GTGGGGCTTC TGCCCGGACC AAGGATACAG
1201  TTTGTTCCTC GTGGCGGCGC ATGAGTTCGG CCACGCGCTG GCTTAGATC ATTCCTCAGT
1261  GCCGGAGGCG CTCATGTACC CTATGTACCG CTTCACTGAG GGGCCCCCCT TGCATAAGGA
1321  CGACGTGAAT GGCATCCGGC ACCTCTATGG TCCTCGCCCT GAACCTGAGC CACGGCCTCC
1381  AACCACCACC ACACCGCAGC CCACGGCTCC CCCGACGGTC TGCCCCACCG ACCCCCCAC
1441  TGTCCACCCC TCAGAGCGCC CCACAGCTGG CCCCACAGGT CCCCCCTCAG CTGGCCCCAC
1501  AGGTCCCCCC ACTGCTGGCC CTTCTACGGC CACTACTGTG CCTTTGAGTC CGGTGGACGA
1561  TGCCTGCAAC GTGAACATCT TCGACGCCAT CGCGGAGATT GGGAACCAGC TGTATTTGTT
1621  CAAGGATGGG AAGTACTGGC GATTCTCTGA GGGCAGGGGG AGCCGGCCGC AGGGCCCCTT
1681  CCTTATCGCC GACAAGTGGC CCGCGCTGCC CCGCAAGCTG GACTCGGTCT TTGAGGAGCC
1741  GCTCTCCAAG AAGCTTTTCT TCTTCTCTGG GCGCCAGGTG TGGGTGTACA CAGGCGCGTC
1801  GGTGCTGGGC CCGAGGCGTC TGGACAAGCT GGGCCTGGGA GCCGACGTGG CCCAGGTGAC
1861  CGGGGCCCTC GGAGTGGCA GGGGGAAGAT GCTGCTGTTC AGCGGGCGGC GCCTCTGGAG
1921  GTTCGACGTG AAGGCGCAGA TGGTGGATCC CCGGAGCGCC AGCGAGGTGG ACCGGATGTT
1981  CCCCGGGGTG CCTTTGGACA CGCACGACGT CTTCCAGTAC CGAGAGAAAG CCTATTTCTG
2041  CCAGGACCGC TTCTACTGGC GCGTGAGTTC CGGAGTGAG TTGAACCAGG TGGACCAAGT
2101  GGGCTACGTG ACCTATGACA TCCTGCAGTG CCCTGAGGAC TAGGGCTCCC GTCCTGCTTT
2161  GCAGTGCCAT GTAAATCCCC ACTGGGACCA ACCCTGGGGA AGGAGCCAGT TGCCGGATA
2221  CAAACTGGTA TTCTGTTCTG GAGGAAAGGG AGGAGTGGAG GTGGGCTGGG CCCTCTCTTC
2281  TCACCTTTGT TTTTGTTGG AGTGTTTCTA ATAAACTTGG ATTCTCTAAC CTTT
```

FIG. 1

```
                                    CAGATTTCCATCAGCAGGATGTGGGGGCTCAAGGTT
                                                     M  W  G  L  K  V
  37  CTGCTGCTACCTGTGGTGAGCTTTGCTCTGTACCCTGAGGAGATACTGGACACCCACTGG
       L  L  L  P  V  V  S  F  A  L  Y  P  E  E  I  L  D  T  H  W
  97  GAGCTATGGAAGAAGACCCACAGGAAGCAATATAACAACAAGGTGGATGAAATCTCTCCC
       E  L  W  K  K  T  H  R  K  Q  Y  N  N  K  V  D  E  I  S  P
 157  CGTTTAATTTGGGAAAAAAACCTGAAGTATATTTCCATCCATAACCTTGAGGCTTCTCTT
       R  L  I  W  E  K  N  L  K  Y  I  S  I  H  N  L  E  A  S  L
 217  GGTGTCCATACATATGAACTGGCTATGAACCACCTGGGGGACATGACCAGTGAAGAGGTG
       G  V  H  T  Y  E  L  A  M  N  H  L  G  D  M  T  S  E  E  V
 277  GTTCAGAAGATGACTGGACTCAAAGTACCCCTGTCTCATTCCCGCAGTAATGACACCCTT
       V  Q  K  M  T  G  L  K  V  P  L  S  H  S  R  S  N  D  T  L
 337  TATATCCCAGAATGGGAAGGTAGAGCCCCAGACTCTGTCGACTATCGAAAGAAAGGATAT
       Y  I  P  E  W  E  G  R  A  P  D  S  V  D  Y  R  K  K  G  Y
 397  GTTACTCCTGTCAAAAATCAGGGTCAGTGTGGTTCCTGTTGGGCTTTTAGCTCTGTGGGT
       V  T  P  V  K  N  Q  G  Q  C  G  S  C  W  A  F  S  S  V  G
 457  GCCCTGGAGGGCCAACTCAAGAAGAAAACTGGCAAACTCTTAAATCTGAGTCCCCAGAAC
       A  L  E  G  Q  L  K  K  K  T  G  K  L  L  N  L  S  P  Q  N
 517  CTAGTGGATTGTGTGTCTGAGAATGATGGCTGTGGAGGGGGCTACATGACCAATGCCTTC
       L  V  D  C  V  S  E  N  D  G  C  G  G  G  Y  M  T  N  A  F
 577  CAATATGTGCAGAAGAACCGGGGTATTGACTCTGAAGATGCCTACCCATATGTGGGACAG
       Q  Y  V  Q  K  N  R  G  I  D  S  E  D  A  Y  P  Y  V  G  Q
 637  GAAGAGAGTTGTATGTACAACCCAACAGGCAAGGCAGCTAAATGCAGAGGGTACAGAGAG
       E  E  S  C  M  Y  N  P  T  G  K  A  A  K  C  R  G  Y  R  E
 697  ATCCCCGAGGGGAATGAGAAAGCCCTGAAGAGGGCAGTGGCCCGAGTGGGACCTGTCTCT
       I  P  E  G  N  E  K  A  L  K  R  A  V  A  R  V  G  P  V  S
 757  GTGGCCATTGATGCAAGCCTGACCTCCTTCCAGTTTTACAGCAAAGGTGTGTATTATGAT
       V  A  I  D  A  S  L  T  S  F  Q  F  Y  S  K  G  V  Y  Y  D
 817  GAAAGCTGCAATAGCGATAATCTGAACCATGCGGTTTTGGCAGTGGGATATGGAATCCAG
       E  S  C  N  S  D  N  L  N  H  A  V  L  A  V  G  Y  G  I  Q
 877  AAGGGAAACAAGCACTGGATAATTAAAAACAGCTGGGGAGAAAACTGGGGAAACAAAGGA
       K  G  N  K  H  W  I  I  K  N  S  W  G  E  N  W  G  N  K  G
 937  TATATCCTCATGGCTCGAAATAAGAACAACGCCTGTGGCATTGCCAACCTGGCCAGCTTC
       Y  I  L  M  A  R  N  K  N  N  A  C  G  I  A  N  L  A  S  F
 997  CCCAAGATGTGACTCCAGCCAGCCAAATCCATCCTGCTCTTCCATTTCTTCCACGATGGT
       P  K  M  ***
1057  GCAGTGTAACGATGCACTTTGGAAGGGAGTTGGTGTGCTATTTTTGAAGCAGATGTGGTG
1117  ATACTGAGATTGTCTGTTCAGTTTCCCCATTTGTTTGTGCTTCAAATGATCCTTCCTACT
1177  TTCGTTCTCTCCACCCATGACCTTTTTCACTGTGGCGATCAGGACTTTCCCTGACAGCTG
1237  TGTACTCTTAGGCTAAGAGATGTGACTACAGCCTGCCCCTGACTGTGTTGTCCCAGGGCT
1297  GATGCTGTACAGGTACAGGCTGGAGATTTTCACATAGGTTAGATTCTCATTCACGGGACT
1357  AGTTAGCTTTAAGCACCCTAGAGGACTAGGGTAATCTGACTTCCTAAGTTCCCTTCTATA
1417  TCCTCAAGGTAGAAATGTCTATGTTTTCTACTCCAATTCATAAATCTATTCATAAGTCTT
1477  TGGTACAAGTTTACATGATAAAAGAAATGTGATTTGTCTTCCCTTCTTTGCACTTTTGA
1537  AATAAAGTATTTATCTCCTGTCTACAGTTTAATAAATAGCATCTAGTACACATCACATTC
1597  AAAAAAAAAAAAAAAAAA
```

FIG. 2

```
CGGCGTGCGCGGACGGGCAGCCAGCAGCGGAGGCGCGGCGCAGCACACCCGGGGACCATG   60
                                                            M   1
GGCTCCATGTTCCGGAGCGAGGAGGTGGCCCTGGTCCAGCTCTTTCTGCCCACAGCGGCT  120
 G  S  M  F  R  S  E  E  V  A  L  V  Q  L  F  L  P  T  A  A   21
GCCTACACCTGCGTGAGTCGGCTGGGCGAGCTGGGCCTCGTGGAGTTCAGAGACCTCAAC  180
 A  Y  T  C  V  S  R  L  G  E  L  G  L  V  E  F  R  D  L  N   41
GCCTCGGTGAGCGCCTTCCAGAGACGCTTTGTGGTTGATGTTTGGCGCTGTGAGGAGCTG  240
 A  S  V  S  A  F  Q  R  R  F  V  V  D  V  W  R  C  E  E  L   61
GAGAAGACCTTCACCTTCCTGCAGGAGGAGGTGCGGCGGGCTGGGCTGGTCCTGCCCCCG  300
 E  K  T  F  T  F  L  Q  E  E  V  R  R  A  G  L  V  L  P  P   81
CCAAAGGGGAGGCTGCCGGCACCCCACCCCGGGACCTGCTGCGCATCCAGGAGGAGACG  360
 P  K  G  R  L  P  A  P  P  P  R  D  L  L  R  I  Q  E  E  T  101
GAGCGCCTGGCCCAGGAGCTGCGGGATGTGCGGGGCAACCAGCAGGCCCTGCGGGCCCAG  420
 E  R  L  A  Q  E  L  R  D  V  R  G  N  Q  Q  A  L  R  A  Q  121
CTGCACCAGCTGCAGCTCCACGCCGCCGTGCTACGCCAGGGCCATGAACCTCAGCTGGCA  480
 L  H  Q  L  Q  L  H  A  A  V  L  R  Q  G  H  E  P  Q  L  A  141
GCCGCCCACACAGATGGGGCCTCAGAGAGGACGCCCCTGCTCCAGGCCCCCGGGGGGCCG  540
 A  A  H  T  D  G  A  S  E  R  T  P  L  L  Q  A  P  G  G  P  161
CACCAGGACCTGAGGGTCAACTTTGTGGCAGGTGCCGTGGAGCCCCACAAGGCCCTGCC  600
 H  Q  D  L  R  V  N  F  V  A  G  A  V  E  P  H  K  A  P  A  181
CTAGAGCGCCTGCTCTGGAGGGCCTGCCGCGGCTTCCTCATTGCCAGCTTCAGGGAGCTG  660
 L  E  R  L  L  W  R  A  C  R  G  F  L  I  A  S  F  R  E  L  201
GAGCAGCCGCTGGAGCACCCCGTGACGGGCGAGCCAGCCACGTGGATGACCTTCCTCATC  720
 E  Q  P  L  E  H  P  V  T  G  E  P  A  T  W  M  T  F  L  I  221
TCCTACTGGGGTGAGCAGATCGGACAGAAGATCCGCAAGATCACGGACTGCTTCCACTGC  780
 S  Y  W  G  E  Q  I  G  Q  K  I  R  K  I  T  D  C  F  H  C  241
CACGTCTTCCCGTTTCTGCAGCAGGAGGAGGCCCGCCTCGGGGCCCTGCAGCAGCTGCAA  840
 H  V  F  P  F  L  Q  Q  E  E  A  R  L  G  A  L  Q  Q  L  Q  261
CAGCAGAGCCAGGAGCTGCAGGAGGTCCTCGGGGAGACAGAGCGGTTCCTGAGCCAGGTG  900
 Q  Q  S  Q  E  L  Q  E  V  L  G  E  T  E  R  F  L  S  Q  V  281
CTAGGCCGGGTGCTGCAGCTGCTGCCGCCAGGGCAGGTGCAGGTCCACAAGATGAAGGCC  960
 L  G  R  V  L  Q  L  L  P  P  G  Q  V  Q  V  H  K  M  K  A  301
GTGTACCTGGCCCTGAACCAGTGCAGCGTGAGCACCACGCACAAGTGCCTCATTGCCGAG 1020
 V  Y  L  A  L  N  Q  C  S  V  S  T  T  H  K  C  L  I  A  E  321
GCCTGGTGCTCTGTGCGAGACCTGCCCGCCCTGCAGGAGGCCCTGCGGGACAGCTCGATG 1080
 A  W  C  S  V  R  D  L  P  A  L  Q  E  A  L  R  D  S  S  M  341
GAGGAGGGAGTGAGTGCCGTGGCTCACCGCATCCCCTGCCGGGACATGCCCCCCACACTC 1140
 E  E  G  V  S  A  V  A  H  R  I  P  C  R  D  M  P  P  T  L  361
ATCCGCACCAACCGCTTCACGGCCAGCTTCCAGGGCATCGTGGATCGCTACGGCGTGGGC 1200
 I  R  T  N  R  F  T  A  S  F  Q  G  I  V  D  R  Y  G  V  G  381
CGCTACCAGGAGGTCAACCCCGCTCCCTACACCATCATCACCTTCCCCTTCCTGTTTGCT 1260
 R  Y  Q  E  V  N  P  A  P  Y  T  I  I  T  F  P  F  L  F  A  401
```

FIG. 3A

```
GTGATGTTCGGGGATGTGGGCCACGGGCTGCTCATGTTCCTCTTCGCCCTGGCCATGGTC   1320
 V  M  F  G  D  V  G  H  G  L  L  M  F  L  F  A  L  A  M  V    421
CTTGCGGAGAACCGACCGGCTGTGAAAGCCGCGCAGAACGAGATCTGGCAGACTTTCTTC   1380
 L  A  E  N  R  P  A  V  K  A  A  Q  N  E  I  W  Q  T  F  F    441
AGGGGCCGCTACCTGCTCCTGCTTATGGGCCTGTTCTCCATCTACACCGGCTTCATCTAC   1440
 R  G  R  Y  L  L  L  L  M  G  L  F  S  I  Y  T  G  F  I  Y    461
AACGAGTGCTTCAGTCGCGCCACCAGCATCTTCCCCTCGGGCTGGAGTGTGGCCGCCATG   1500
 N  E  C  F  S  R  A  T  S  I  F  P  S  G  W  S  V  A  A  M    481
GCCAACCAGTCTGGCTGGAGTGATGCATTCCTGGCCCAGCACACGATGCTTACCCTGGAT   1560
 A  N  Q  S  G  W  S  D  A  F  L  A  Q  H  T  M  L  T  L  D    501
CCCAACGTCACCGGTGTCTTCCTGGGACCCTACCCCTTTGGCATCGATCCTATTTGGAGC   1620
 P  N  V  T  G  V  F  L  G  P  Y  P  F  G  I  D  P  I  W  S    521
CTGGCTGCCAACCACTTGAGCTTCCTCAACTCCTTCAAGATGAAGATGTCCGTCATCCTG   1680
 L  A  A  N  H  L  S  F  L  N  S  F  K  M  K  M  S  V  I  L    541
GGCGTCGTGCACATGGCCTTTGGGGTGGTCCTCGGAGTCTTCAACCACGTGCACTTTGGC   1740
 G  V  V  H  M  A  F  G  V  V  L  G  V  F  N  H  V  H  F  G    561
CAGAGGCACCGGCTGCTGCTGGAGACGCTGCCGGAGCTCACCTTCCTGCTGGGACTCTTC   1800
 Q  R  H  R  L  L  L  E  T  L  P  E  L  T  F  L  L  G  L  F    581
GGTTACCTCGTGTTCCTAGTCATCTACAAGTGGCTGTGTGTCTGGGCTGCCAGGGCCGCC   1860
 G  Y  L  V  F  L  V  I  Y  K  W  L  C  V  W  A  A  R  A  A    601
TCGCCCAGCATCCTCATCCACTTCATCAACATGTTCCTCTTCTCCCACAGCCCCAGCAAC   1920
 S  P  S  I  L  I  H  F  I  N  M  F  L  F  S  H  S  P  S  N    621
AGGCTGCTCTACCCCCGGCAGGAGGTGGTCCAGGCCACGCTGGTGGTCCTGGCCTTGGCC   1980
 R  L  L  Y  P  R  Q  E  V  V  Q  A  T  L  V  V  L  A  L  A    641
ATGGTGCCCATCCTGCTGCTTGGCACACCCCTGCACCTGCTGCACCGCCACCGCCGCCGC   2040
 M  V  P  I  L  L  L  G  T  P  L  H  L  L  H  R  H  R  R  R    661
CTGCGGAGGAGGCCCGCTGACCGACAGGAGGAAAACAAGGCCGGGTTGCTGGACCTGCCT   2100
 L  R  R  R  P  A  D  R  Q  E  E  N  K  A  G  L  L  D  L  P    681
GACGCATCTGTGAATGGCTGGAGCTCCGATGAGGAAAAGGCAGGGGCCTGGATGATGAA   2160
 D  A  S  V  N  G  W  S  S  D  E  E  K  A  G  G  L  D  D  E    701
GAGGAGGCCGAGCTCGTCCCCTCCGAGGTGCTCATGCACCAGGCCATCCACACCATCGAG   2220
 E  E  A  E  L  V  P  S  E  V  L  M  H  Q  A  I  H  T  I  E    741
TTCTGCCTGGGCTGCGTCTCCAACACCGCCTCCTACCTGCGCCTGTGGGCCCTGAGCCTG   2280
 F  C  L  G  C  V  S  N  T  A  S  Y  L  R  L  W  A  L  S  L    741
GCCCACGCCCAGCTGTCCGAGGTTCTGTGGGCCATGGTGATGCGCATAGGCCTGGGCCTG   2340
 A  H  A  Q  L  S  E  V  L  W  A  M  V  M  R  I  G  L  G  L    761
GGCCGGGAGGTGGGCGTGGCGGCTGTGGTGCTGGTCCCCATCTTTGCCGCCTTTGCCGTG   2400
 G  R  E  V  G  V  A  A  V  V  L  V  P  I  F  A  A  F  A  V    781
ATGACCGTGGCTATCCTGCTGGTGATGGAGGGACTCTCAGCCTTCCTGCACGCCCTGCGG   2460
 M  T  V  A  I  L  L  V  M  E  G  L  S  A  F  L  H  A  L  R    801
CTGCACTGGGTGGAATTCCAGAACAAGTTCTACTCAGGCACGGGCTACAAGCTGAGTCCC   2520
 L  H  W  V  E  F  Q  N  K  F  Y  S  G  T  G  Y  K  L  S  P    821
TTCACCTTCGCTGCCACAGATGACTAGGGCCCACTGCAGGTCCTGCCAGACCTCCTTCCT   2580
 F
GACCTCTGAGGCAGGAGAGGAATAAAGACGGTCCGCCCTGGCAAAAAAAAAAAAAAAAAA   2640
```

FIG. 3B

HUMAN OSTEOCLAST-SPECIFIC AND -RELATED DNA SEQUENCES

RELATED APPLICATIONS

This application is a continuation-in-part of U.S. application Ser. No. 08/392,678, filed Feb. 23, 1995, now U.S. Pat. No. 5,552,281, which is a file wrapper continuation of U.S. application Ser. No. 08/045,270, filed Apr. 6, 1993 now abandoned, and U.S. application Ser. No. 08/605,378 now abandoned, filed Feb. 22, 1996. This application also claims priority to co-pending U.S. Provisional Application Serial No. 60/001,292, filed Jul. 20, 1995. The teachings of these prior applications are incorporated herein by reference in their entirety.

GOVERNMENT FUNDING

Work described herein was supported by National Institutes of Health grant numbers DE-07378 and 1K16-0027501 awarded by the National Institute of Dental Research. The U.S. Government has certain rights in the invention.

BACKGROUND OF THE INVENTION

Osteoclasts are multinucleated giant cells specialized for the removal of both the inorganic and organic phases of bone (Blair H. C., et al., *J. Cell. Biol.*, 102:1164–1172 (1986)). The pathway(s) for degradation of the organic matrix, primarily type 1 collagen, are not well understood, although mounting evidence has implicated cysteine proteinases (cathepsins) as key enzymes in this process.

Dissolution of the hydroxyapatite mineral phase is dependent upon acidification of the subosteoclastic resorption lacuna, via the action of carbonic anhydrase II and a proton pump (Vaes, *J. Cell Biol.*, 39:676–697 (1968); Baron et al., *J. Cell Biol.*, 101:2210–2222 (1985); and Blair and Schlesinger, in *Biology and Physiology of the Osteoclast*, Rifkin and Gay, eds. (CRC Press, Boca Raton), pp. 259–287 (1992)). V-type proton pumps are multi-subunit complexes with two distinct functional domains: a peripherally-associated cytoplasmic catalytic sector that contains 70- (subunit A), 58- (subunit B), 40- and 33-kDa (subunit E) subunits (Xie and Stone, *J. Biol. Chem.*, 263:9859–9866 (1988)), and a proton channel, which is likely composed of 116-, 39-, and 17-kDa components (Crider et al., *J. Biol. Chem.*, 269:17379–17381 (1994)). Considerable speculation has focused on the possibility that osteoclast-specific proton pump subunits exist.

Excessive bone resorption by osteoclasts contributes to the pathology of many human diseases including arthritis, osteoporosis, periodontitis, and hypercalcemia of malignancy. During resorption, osteoclasts remove both the mineral and organic components of bone (Blair, H. C., et al., *J. Cell Biol*; 102:1164 (1986)).

The regulation of osteoclastic activity is only partly understood. The lack of information concerning osteoclast function is due in part to the fact that these cells are extremely difficult to isolate as pure populations in large numbers. Furthermore, there are no osteoclastic cell lines available. An approach to studying osteoclast function that permits the identification of heretofore unknown osteoclast-specific or -related DNA sequences, genes and gene products would allow identification of genes and gene products that are involved in the resorption of bone and in the regulation of osteoclastic activity. Therefore, identification of osteoclast-specific or -related DNA sequences, genes or gene products would prove useful in developing therapeutic strategies for the treatment of disorders involving aberrant bone resorption.

SUMMARY OF THE INVENTION

The present invention relates to isolated osteoclast-specific or -related DNA sequences. These sequences can be all or a portion of an osteoclast-specific or -related gene. The sequences of the present invention encode all or a portion of an osteoclast-specific or -related gene product (i.e., peptide or protein) or encode all or a portion of the untranslated portion of the genomic DNA sequence. The present invention further relates to DNA constructs capable of replicating osteoclast-specific or -related DNA. In another embodiment, the invention relates to a DNA construct capable of directing expression of osteoclast-specific or -related DNA sequences, producing osteoclast-specific or -related peptides or gene products, in a host cell.

Also encompassed by the present invention are prokaryotic or K]d cells transformed or transfected with a DNA construct comprising an osteoclast-specific or -related DNA sequence. According to a particular embodiment, these cells are capable of replicating the DNA construct comprising the osteoclast-specific or -related DNA, and, optionally, are capable of expressing the osteoclast-specific or -related peptide or gene product encoded by the osteoclast-specific or -related DNA sequence. Also described are antibodies raised against osteoclast-specific or -related gene products, or portions of these gene products, and osteoclast-specific or -related DNA sequences.

The present invention further embraces a method of identifying osteoclast-specific or -related DNA sequences and DNA sequences identified in this manner. In one embodiment, osteoclast-specific or -related cDNA is identified as follows: first, human giant cell tumor of the bone is used to 1) construct a cDNA library; 2) produce $^{32}$P-labelled cDNA to use as a stromal cell$^+$, osteoclast$^+$ probe, and 3) produce (by culturing) a stromal cell population lacking osteoclasts. The presence of osteoclasts in the giant cell tumor can be confirmed by histological staining for the osteoclast marker, type 5 tartrate-resistant acid phosphatase (TRAP) and/or with the use of monoclonal antibody reagents.

As described herein, the stromal cell population lacking osteoclasts was produced by dissociating cells of a giant cell tumor, then growing and passaging the cells in tissue culture until the cell population was homogeneous and appeared fibroblastic. The cultured stromal cell population did not contain osteoclasts. The cultured stromal cells were then used to produce a stromal cell$^+$, osteoclast$^-$ $^{32}$P-labelled cDNA probe.

The cDNA library produced from the giant cell tumor of the bone was then screened in duplicate for hybridization to the cDNA probes: one screen was performed with the giant cell tumor cDNA probe (stromal cell$^+$, osteoclast$^+$), while a duplicate screen was performed using the cultured stromal cell cDNA probe (stromal cell$^+$, osteoclast$^-$). Hybridization to a stromal$^+$, osteoclast$^+$ probe, accompanied by failure to hybridize to a stromal$^+$, osteoclast$^-$ probe indicated that a clone contained nucleic acid sequences specifically expressed by osteoclasts. That is, the clone contained a nucleic acid sequence which is either uniquely expressed by osteoclasts (i.e., osteoclast-specific) or expressed by osteoclasts and select other cells (i.e., osteoclast-related).

In the course of these studies, four clones were identified which contained DNA sequences with significant homology to portions of DNA sequences encoding cysteine proteases, The structural characterization of the coding region cDNA for a particular enzyme, cathepsin X, from which these four sequences originate is also described herein. The present studies also identified one clone which contained a DNA sequence which is a portion of a-DNA sequence encoding a novel human 116-kDa polypeptide subunit of the osteoclast proton pump (OC-116KDa). OC-116KDa mRNA was found at high levels in giant cells of osteoclastomas by Northern analysis but was not detected in tumor stromal cells or in other tissues including kidney, liver, skeletal muscle and brain. OC-116KDa mRNA was localized to multinucleated giant cells within the osteoclastoma tumor by in situ hybridization. Thus, it. appears that OC-116kDa represents a novel human 116-kDa subunit of a proton pump which is expressed in osteoclasts in a cell-specific manner, In another embodiment of the invention, osteoclast-specific or -related genomic DNA is identified through. known hybridization techniques or amplification techniques. This genomic DNA encodes all or a portion of osteoclast-specific or -related peptides or gene products, or encodes all or a portion of the untranslated region of the gene. In one embodiment, the present invention relates to a method of identifying osteoclast-specific or -related DNA by screening a cDNA library or a genomic DNA library with a DNA probe comprising one or more sequences selected from the group consisting of the DNA sequences set out in Table I (SEQ ID NOS: 1–32). Finally, the present invention relates to a nucleotide sequence comprising a DNA sequence selected from the group consisting of the sequences set out in Table I, or their complementary strands, and to peptides or proteins encoded thereby.

The polypeptides and proteins of the present invention have utility as osteodlast cell surface markers. expression of the described polypeptides or proteins is characteristic of osteoclasts, and is unlikely to be found in a wide variety of other cells. Thus, these proteins can be labelled, e.g., radioactively or fluorescently, and used as cell surface markers for osteoclasts.

BRIEF DESCRIPTION OF THE DRAWINGS

FIG. 1 shows the cDNA sequence (SEQ ID NO: 33) of, human gelatinase B. The portions of the sequence represented by the osteoclast-specific or -related cDNA clones of the present invention are underlined.

FIG. 2 shows the complete nucleotide sequence (SEQ ID NO: 35) and deduced amino acid sequence (SEQ ID NO: 36) of cathepsin X. Those portions of the sequence represented by the osteoclast-specific or -related cDNA clones (SEQ ID NOS: 7, 24, 18 and 16, respectively) of the present invention are underlined.

FIGS. 3A and 3B represent the nucleotide sequence (SEQ ID NO: 37) and deduced amino acid sequence (SEQ ID NO: 38) of human OC-116KDa. Those portions of the sequence represented by the osteoclast-specific or -related cDNA clones (SEQ ID NO: 25) of the present invention are underlined.

DETAILED DESCRIPTION OF THE INVENTION

As described herein, osteoclast-specific or osteoclast-related nucleic acid sequences have been identified. These sequences were identified as follows: human giant cell tumor of the bone was used to 1) construct a cDNA library; 2) produce $^{32}$P-labelled cDNA to use as a stromal cell$^+$, osteoclast$^+$ probe, and 3) produce (by culturing) a stromal cell population lacking osteoclasts. The presence of osteoclasts in the giant cell tumor was confirmed by histological staining for the osteoclast marker, type 5 acid phosphatase (TRAP). In addition, monoclonal antibody reagents were used to characterize the multinucleated cells in the giant cell tumor, which cells were found to have a phenotype distinct from macrophages and consistent with osteoclasts.

The stromal cell population lacking osteoclasts was produced by dissociating cells of a giant cell tumor, then growing the cells in tissue culture for at least five passages. After five passages the cultured cell population was homogeneous and appeared fibroblastic. The cultured population contained no multinucleated cells at this point, tested negative for type 5 acid phosphatase, and tested variably alkaline phosphatase positive. That is, the cultured stromal cell population did not contain osteoclasts. The cultured stromal cells were then used to produce a stromal cell$^+$, osteoclast$^{-32}$P-labelled cDNA probe.

The cDNA library produced from the giant cell tumor of the bone was then screened in duplicate for hybridization to the cDNA probes: one screen was performed with the giant cell tumor cDNA probe (stromal cell$^+$, osteoclast$^+$), while a duplicate screen was performed using the cultured stromal cell cDNA probe (stromal cell$^+$, osteoclast$^-$). Clones that hybridized to the giant cell tumor cDNA probe (stromal$^+$, osteoclast$^+$), but not to the stromal cell cDNA probe (stromal$^+$, osteoclast$^-$), were considered to contain nucleic acid sequences specifically expressed by osteoclasts. That is, the clones contained nucleic acid sequences which are either uniquely expressed by osteoclasts (i.e., "osteoclast-specific) or expressed by osteoclasts (i.e., select other cells (i.e., osteoclast-related).

As a result of the differential screen described herein, DNA specifically expressed in osteoclast cells characterized as described herein was identified. This DNA and equivalent DNA sequences are referred to herein as "osteoclast-specific" or "osteoclast-related DNA". Osteoclast-specific or -related DNA of the present invention can be obtained from sources in which it occurs in nature, can be produced recombinantly or synthesized chemically; it can be cDNA, genomic DNA, recombinantly-produced DNA or chemically-produced DNA. An equivalent DNA sequence is one which hybridizes, "under standard (i.e., medium stringency) hybridization conditions", to an "osteoclast-specific or -related DNA" identified as described herein or to a complement thereof. Stringency conditions which are appropriately termed "medium stringency" are known to those skilled in the art or can, be found in standard texts such as *Current Protocols in Molecular Biology*, John Wiley & Sons, N.Y. (1989), 6.3.1–6.3.6.

Differential screening of a human osteoclastoma cDNA library was performed to identify DNA sequences and genes specifically expressed in osteoclasts. Of 12,000 clones screened, 195 clones were identified which are either uniquely expressed in osteoclasts (i.e., osteoclast-specific), or are expressed by osteoclasts and select other cells (osteoclast-related). These clones were also negative when screened with mixed cDNA probes derived from a panel of human cell lines, including myelomonocytic (U-937), T lymphocyte (HSB-2), epithelial (laryngeal carcinoma HEp-2), neuroblastoma (SK-N-MC), pancreatic adenocarcinoma (AsPC-1), normal skin fibroblasts (CRL 1467) and osteoblasts, further supporting the osteoclast-specificity of these sequences. Of these 195 clones, 32 contained novel cDNA sequences which were not found in the GenBank database.

A large number of the 195 DNA clones obtained by this procedure were found to represent 92 kDa type IV collagenase (gelatinase B; E.C. 3.4.24.35) as well as tartrate resistant acid phosphatase (TRAP). In situ hybridization localized mRNA for gelatinase B to multinucleated giant cells in human osteoclastomas.

Gelatinase B immunoreactivity was demonstrated in giant cells from 8/8 osteoclastomas, osteoclasts in normal bone, and in osteoclasts of Paget's disease by use of a polyclonal antisera raised against a synthetic gelatinase B peptide. In contrast, no immunoreactivity for 72 kDa type IV collagenase (gelatinase A; E.C. 3.4.24.24), which is the product of a separate gene, was detected in osteoclastomas or normal osteoclasts.

In addition, four clones (SEQ ID NOS: 7, 16, 18 and 24) were identified which were confirmed to be part of a DNA sequence which possessed significant homology to cathepsins from human and other species but was not identical to any known cathepsin. Northern analysis of mRNA from the osteoclastoma tumor using a $^{32}$P-labeled cathepsin X probe revealed a transcript of approximately 1.9 kb. Cathepsin X mRNA was found at high levels in osteoclastoma tumor but was not detected in skeletal muscle, liver, or brain. Cathepsin X mRNA was also absent from osteoclastoma stromal cells as well as human cell lines U-937, HOS-TE85 (osteosarcoma), HSB-2, Hep-2, SK-N-MC, and AsPC-1. Rescreening the pcDNAII library failed to yield clones containing full-length inserts.

Consequently, a second osteoclastoma library constructed in lambda-ZAP yielded 40 positive clones, two of which contained inserts of greater than 1.6 kb.

Cells within the osteoclastoma that produce mRNA for cathepsin X were identified by in situ hybridization. A digoxygenin-labeled antisense probe was strongly reactive with all multinucleated osteoclasts but was unreactive with most stromal cells. In contrast, the sense probe produced only minimal background staining, which was not localized to any cell type. It was noted that a small number of mononuclear cells, possibly osteoclast precursors, also stained positively with the antisense probe. In situ hybridization with a second osteoclastoma tumor yielded an identical result.

The complete nucleotide (SEQ ID NO: 35) and deduced amino acid sequence (SEQ ID NO: 36) of cathepsin X are presented in FIG. 2. Cathepsin X appears to represent the human homolog of the osteoclast-expressed rabbit cathepsin OC-2 described by Tezuka et al. (Tezuka, K. et al., *J. Bio. Chem.*, 269:1106–1109 (1994)). Cathepsin X is 93.9% similar to OC-2 at the amino acid level and 92% homologous at the nucleotide level within the coding region.

Because work described herein focused initially on clones producing strong signals with the mixed cDNA tumor$^+$ probe in the differential screening step, DNA sequences identified herein are expressed at relatively high levels in osteoclasts, such as TRAP, gelatinase B, and cathepsin X. The high mRNA levels for cathepsin X in osteoclasts was further confirmed by strong Northern blot and the in situ hybridization signals generated. Since neither cathepsin L nor B was identified by this approach, it appears that cathepsin X is uniquely expressed by osteoclasts and not by other cell types within this tumor.

In addition, one clone (SEQ ID NO: 25) Which gave a positive hybridization signal with tumor cDNA, but was negative with stromal cell cDNA, was found to possess approximately 60% homology to the rat 116-kDA vacuolar type-proton pump subunit, but was not identical to any known proton pump subunit. This clone was designated OC-116KDa and was confirmed to be part of a DNA sequence encoding a novel human osteoclast proton pump 116-kDa subunit (OC-116KDa).

Northern analysis of mRNA from the osteoclastoma tumor using an $\alpha^{32}$P-labelled 1.0 kb 3' OC-116KDa cDNA probe revealed a transcript of approximately 2.7 kb. A 0.5 kb probe from the 5' end of OC-116 kDa gave the same result (data not shown). OC-116KDa mRNA was found at high levels in the osteoclastoma tumor, and at much lower levels in the human pancreatic adenocarcinoma cell line (AsPC-1), but was not detected in skeletal muscle, liver, kidney, or brain. OC-116KDa mRNA was also absent from osteoclastoma stromal cells, normal rat osteoblasts (ROB), as well as a panel of human cell lines: osteoblastic (HOS-TE85), myelomonocytic (U-937), T lymphocyte (HSB-2), epithelial (laryngeal carcinoma HEp-2), neuroblastoma (SK-N-MC), and normal skin fibroblasts (CRL 1467).

Rescreening the pcDNAII library failed to yield clones containing full-length inserts. A second library was therefore constructed in phage using the Lambda-ZAP system (Stratagene). This library consisted of ~6×10$^5$ clones of average insert length 1.0 kb. Screening of this library yielded 25 positive clones, of which the two longest (p-18 and p-43) contained inserts of greater than 2.6 kb. Complete bidirectional sequence analysis was carried on the p-43 clone. Four other clones including p-18 were partially sequenced. All sequences were identical.

The nucleotide sequence (SEQ ID NO: 37) and the deduced amino acid sequence (SEQ ID NO: 38) of the OC-116KDa cDNA clone are shown in FIGS. 3A and 3B. Database searches revealed that OC-116KDa shows 59.4% homology at the nucleotide level with the rat 116-kDa subunit of the clathrin-coated vesicle proton pump and 59.1% homology with the bovine brain 116-kDa subunit vacuolar proton pump. OC-116KDa exhibits 46.9% and 47.2% homology at the amino acid level with-the rat 116KDa polypeptide and the bovine 116KDa polypeptide, respectively (Perin et al., *J. Biol. Chem.* 266:3877–3881 (1991); Peng et al., *J. Biol. Chem.* 269:17262–17266 (1994)).

The present invention has utility for the production and identification of nucleic acid probes useful for identifying osteoclast-specific or -related DNA. Osteoclast-specific or -related DNA of the present invention can be used to produce osteoclast-specific or -related gene products useful in the therapeutic treatment or diagnosis of disorders involving aberrant bone resorption.

The osteoclast-specific or -related sequences are also useful for generating peptides which can then be used to produce antibodies useful for identifying osteoclast-specific or -related peptides or gene products, or for altering the activity of osteoclast-specific or -related gene products. Such antibodies are referred to as osteoclast-specific antibodies.

Osteoclast-specific antibodies are also useful for identifying osteoclasts. For instance, polyclonal and monoclonal antibodies which bind to a polypeptide or protein encoded by the described osteoclast-specific or -related DNA sequences are within the scope of the invention. A mammal, such as a mouse, hamster or rabbit, can be immunized with an immunogenic form of the polypeptide (i.e., an antigenic portion of the polypeptide which is capable of eliciting an antibody response). Techniques for conferring immunogenicity on a protein or peptide include conjugation to carriers or other techniques well known in the art. The protein or polypeptide can be administered in the presence of an adjuvant. The progress of immunization can be monitored by detection of antibody titers in plasma or serum. Standard ELISA or other immunoassays can be used with the immunogen as antigen to assess the levels of antibody.

Following immunization, anti-peptide antisera can be obtained, and if desired, polyclonal antibodies can be isolated from the serum. Monoclonal antibodies can also be produced by standard techniques which are well known in the art (Kohler and Milstein, *Nature* 256:495–497 (1975); Kozbar et al., *Immunology Today* 4:72 (1983); and Cole et al., *Monoclonal Antibodies and Cancer Therapy*, Alan R. Liss, Inc., pp. 77–96 (1985)).

The invention also provides expression vectors and constructs containing the osteoclast-specific or -related nucleic acid sequences, encoding an osteoclast-specific or -related peptide or protein, operably linked to at least one regulatory sequence. "Operably linked" is intended to mean that the nucleotide sequence is linked to a regulatory sequence in a manner which allows expression of the nucleic acid sequence. Regulatory sequences are art-recognized and include promoters, enhancers, and other expression control elements which are described in Goeddel, Gene Expression Technology: *Methods in Enzymology* 185, Academic Press, San Diego, Calif. (1990). It should be understood that the design of the expression vector may depend on such factors as the choice of the host cell to be transformed and/or the type of peptide or protein desired to be expressed. For instance, peptides encoded by the DNA sequences of the present invention can be produced by ligating the cloned DNA sequence, or a portion thereof, into a vector suitable for expression in either prokaryotic cells, K cells or both (see, for example, Broach, et al., *Experimental Manipulation of Gene Expression*, ed. M. Inouye (Academic Press, 1983) p. 83; *Molecular Cloning: A Laboratory Manual*, 2nd Ed., ed. Sambrook et al. (Cold Spring Harbor Laboratory Press, 1989) Chapters 16 and 17).

Prokaryotic and K host cells transfected by the described vectors are also provided by this invention. For instance, cells which can be transfected with the vectors of the present invention include, but are not limited to, bacterial cells such as *E. coli*, insect cells (baculovirus), yeast or mammalian cells such as Chinese hamster ovary cells (CHO).

Thus, the osteoclast-specific or -related nucleotide sequences described herein can be used to produce a recombinant form of an osteoclast-specific or -related peptide or protein, or portion thereof, via microbial or K cellular processes. Ligating the polynucleotide sequence into a gene construct, such as an expression vector, and transforming or transfecting into hosts, either K (yeast, avian, insect or mammalian) or prokaryotic (bacterial cells), are standard procedures. Similar procedures, or modifications thereof, can be employed to prepare recombinant peptides or proteins according to the present invention by microbial means or tissue-culture technology.

Finally, osteoclast -specific or -related DNA sequences of the present invention are useful in gene therapy. For example, they can be used to alter the expression in osteoclasts of an aberrant osteoclast-specific or -related gene product or to correct aberrant expression of an osteoclast-specific or -related gene product. The sequences described herein can further be used to cause osteoclast-specific or -related gene expression in cells in which such expression does not ordinarily occur, i.e., in cells which are not osteoclasts.

The following Examples are offered for the purpose of illustrating the present invention and are not to be construed to limit the scope of this invention. The teachings of all references cited herein are hereby incorporated herein by reference.

EXAMPLE 1

Osteoclast cDNA Library Construction

Messenger RNA (mRNA) obtained from a human osteoclastoma ('giant cell tumor of bone'), was used to construct an osteoclastoma cDNA library. Osteoclastomas are actively bone resorptive tumors, but are usually non-metastatic. In cryostat sections, osteoclastomas consist of ~30% multinucleated cells positive for tartrate resistant acid phosphatase (TRAP), a widely utilized phenotypic marker specific in vivo for osteoclasts (Minkin, *Calcif. Tissue Int.* 34:285–290 (1982)). The remaining cells are uncharacterized 'stromal' cells, a mixture of cell types with fibroblastic/mesenchymal morphology. Although it has not yet been definitively shown, it is generally held that the osteoclasts in these tumors are non-transformed, and are activated to resorb bone in vivo by substance(s) produced by the stromal cell element.

Monoclonal antibody reagents were used to partially characterize the surface phenotype of the multinucleated cells in the giant cell tumors of long bone. In frozen sections, all multinucleated cells expressed CD68, which has previously been reported to define an antigen specific for both osteoclasts and macrophages (Horton, M. A. and M. H. Helfrich, In Biology and Physiology of the Osteoclast, B. R. Rifkin and C. V. Gay, editors, CRC Press, Inc. Boca Raton, Fla., 33–54 (1992)). In contrast, no staining of giant cells was observed for CD11b or CD14 surface antigens, which are present on monocyte/macrophages and granulocytes (Arnaout, M. A. et al. *J. Cell. Physiol.* 137:305 (1988); Haziot, A. et al. *J. Immunol.* 141:547 (1988)). Cytocentrifuge preparations of human peripheral blood monocytes were positive for CD68, CD11b, and CD14. These results demonstrate that the multinucleated giant cells of osteoclastomas have a phenotype which is distinct from that of macrophages, and which is consistent with that of osteoclasts.

Osteoclastoma tissue was snap frozen in liquid nitrogen and used to prepare poly $A^+$ mRNA according to standard methods. cDNA cloning into a pcDNAII vector was carried out using a commercially-available kit (Librarian, InVitrogen). Approximately $2.6 \times 10^6$ clones were obtained, greater than 95% of which contained inserts of an average length 0.6 kB.

EXAMPLE 2

Stromal Cell mRNA Preparation

A portion of each osteoclastoma was snap frozen in liquid nitrogen for mRNA preparation. The remainder of the tumor was dissociated using brief trypsinization and mechanical disaggregation, and placed into tissue culture. These cells were expanded in Dulbecco's MEM (high glucose, Sigma) supplemented with 10% newborn calf serum (MA Bioproducts), gentamycin (0.5 mg/ml), 1-glutamine (2 mM)

and non-essential amino acids (0.1 mM) (Gibco). The stromal cell population was passaged at least five times, after which it showed a homogenous, fibroblastic looking cell population that contained no multinucleated cells. The stromal cells were mononuclear, tested negative for acid phosphatase, and tested variably alkaline phosphatase positive. These findings indicate that propagated stromal cells (i.e., stromal cells that are passaged in culture) are non-osteoclastic and non-activated.

EXAMPLE 3

Identification of Osteoclast-Specific or -Related DNA Sequences by Differential Screening of an Osteoclastoma cDNA Library A total of 12,000 clones drawn from the osteoclastoma cDNA library were screened by differential hybridization, using mixed $^{32}$P labelled cDNA probes derived from (1) giant cell tumor mRNA (stromal cell$^+$, OC$^+$), and (2) mRNA from stromal cells (stromal cell$^+$, OC$^-$) cultivated from the same tumor. The probes were labelled with $^{32}$[P]dCTP by random priming to an activity of ~$10^9$CPM/μg. Of these 2,000 clones, 195 gave a positive hybridization signal with giant cell (i.e., osteoclast and stromal cell) mRNA, but not with stromal cell mRNA. Additionally, these clones failed to hybridize to cDNA produced from mRNA derived from a variety of unrelated human cell types including epithelial cells, fibroblasts, lymphocytes, myelomonocytic cells, osteoblasts, and neuroblastoma cells. The failure of these clones to hybridize to cDNA produced from mRNA derived from other cell types supports the conclusion that these clones are either uniquely expressed in osteoclasts or are osteoclast-related.

The osteoclast (OC) cDNA library was screened for differential hybridization to OC cDNA (stromal cell$^+$, OC$^+$) and stromal cell cDNA (stromal cell$^+$, OC$^-$) as follows:

NYTRAN filters (Schleicher & Schuell) were placed on agar plates containing growth medium and ampicillin. Individual bacterial colonies from the OC library were randomly picked and transferred, in triplicate, onto filters with preruled grids and then onto a master agar plate. Up to 200 colonies were inoculated onto a single 90-mm filter/plate using these techniques. The plates were inverted and incubated at 37° C. until the bacterial inoculates had grown (on the filter) to a diameter of 0.5–1.0 mm.

The colonies were then lysed, and the DNA bound to the filters by first placing the filters on top of two pieces of Whatman 3MM paper saturated with 0.5 N NaOH for 5 minutes. The filters were neutralized by placing on two pieces of Whatman 3MM paper saturated with 1 M Tris-HCL, pH 8.0 for 3–5 minutes. Neutralization was followed by incubation on another set of Whatman 3MM papers saturated with 1M Tris-HCL, pH 8.0/1.5 M NaCl for 3–5 minutes. The filters were then washed briefly in 2xSSC.

DNA was immobilized on the filters by baking the filters at 80° C. for 30 minutes. Filters were best used immediately, but they could be stored for up to one week in a vacuum jar at room temperature.

Filters were prehybridized in 5–8 ml of hybridization solution per filter, for 2–4 hours in a heat sealable bag. An additional 2 ml of solution was added for each additional filter added to the hybridization bag. The hybridization buffer consisted of 5xSSC, 5xDenhardt's solution, 1xSDS and 100 μg/ml denatured heterologous DNA.

Prior to hybridization, labeled probe was denatured by heating in 1xSSC for 5 minutes at 100° C., then immediately chilled on ice. Denatured probe was added to the filters in hybridization solution, and the filters hybridized with continuous agitation for 12–20 hours at 65° C.

After hybridization, the filters were washed in 2xSSC/0.2% SDS at 50–60° C. for 30 minutes, followed by washing in 0.2xSSC/0.2% SDS at 60° C. for 60 minutes.

The filters were then air dried and autoradiographed using an intensifying screen at –70° C. overnight.

EXAMPLE 4

DNA Sequencing of Selected Clones

Clones reactive with the mixed tumor probe, but unreactive with the stromal cell probe, are expected to contain either osteoclast-specific or -related DNA sequences. One hundred forty-four of the 195 cDNA clones that hybridized to tumor cell cDNA, but not to stromal cell cDNA, were sequenced by the dideoxy chain termination method of Sanger et al. (Sanger F., et al. *Proc. Natl. Acad. Sci. USA* 74:5463 (1977)) using sequenase (US Biochemical). The DNASIS (Hitatchi)-program was used to carry out sequence analysis and a homology search in the GenBank/EMBL database. Fourteen of the 195 tumor$^+$ stromal$^-$ clones were identified as containing inserts with a sequence identical to the osteoclast marker, type 5 tartrate-resistant acid phosphatase (TRAP) (GenBank accession number J04430 M19534). The high representation of TRAP positive clones indicates the effectiveness of the screening procedure in enriching for clones which contain osteoclast-specific or -related cDNA sequences.

Interestingly, an even larger proportion of the tumor$^+$ stromal$^-$ clones (77/195; 39.5;) were identified as human gelatinase B (macrophage-derived gelatinase) (Wilhelm, S. M. *J. Biol. Chem.* 264:17213 (1989)), again indicating high expression of this enzyme by osteoclasts. Twenty-five of the gelatinase B clones were identified by dideoxy sequence analysis; all 25 showed 100% sequence homology to the published gelatinase B sequence (Genbank accession number J05070). The portions of the gelatinase B cDNA sequence corresponding to these clones is shown in FIG. 1 (SEQ ID NO: 33). An additional 52 gelatinase B clones were identified by reactivity with a $^{32}$P-labelled probe for gelatinase B.

Thirteen of the sequenced clones yielded no readable sequence. A DNASIS search of GenBank/EMBL databases revealed that, of the remaining 91 clones, 31 clones contained novel sequences which have not yet been reported in the databases or in the literature. These partial sequences are presented in Table I. Note that three of these sequences were repeats, indicating fairly frequent representation of mRNA related to this sequence. The repeat sequences are indicated by $^a$, $^b$, superscripts (Clones 198B, 223B and 32C of Table I). One additional sequence was identified (Clone 28B) which appeared novel but which was found to have been previously reported. The sequence contained in this clone was:

```
                                           (SEQ ID NO: 4)
TTTTATTTGT AAATATATGT ATTACATCCC TAGAAAAAGA

ATCCCAGGAT TTTCCCTCCT GTGTGTTTTC GTCTTGCTTC

TTCATGGTCC ATGATGCCAG CTGAGGTTGT CAGTACAATG

AAACCAAACT GGCGGGATGG AAGCAGATTA TTCTGCCATT

TTTCCAGGTC TTT.
```

TABLE I

SEQUENCES OF 31 NOVEL OC-SPECIFIC OR -RELATED
cDNA CLONES 34A (SEQ ID NO: 1)
1     GCAAATATCT AAGTTTATTG CTTGGATTTC TAGTGAGAGC TGTTGAATTT GGTGATGTCA
61    AATGTTTCTA GGGTTTTTTT AGTTTGTTTT TATTGAAAAA TTTAATTATT TATGCTATAG
121   GTGATATTCT CTTTGAATAA ACCTATAATA GAAAATAGCA GCAGACAACA 4B (SEQ ID NO: 2)
1     GTGTCAACCT GCATATCCTA AAAATGTCAA AATGCTGCAT CTGGTTAATG TCGGGGTAGG
61    GGG 12B (SEQ ID NO: 3)
1     CTTCCCTCTC TTGCTTCCCT TTCCCAAGCA GAGGTGCTCA CTCCATGGCC ACCGCCACCA
61    CAGGCCCACA GGGAGTACTG CCAGACTACT GCTGATGTTC TCTTAAGGCC CAGGGAGTCT
121   CAACCAGCTG GTGGTGAATG CTGCCTGGCA CGGGACCCCC CCC 37B (SEQ ID NO: 5)
1     GGCTGGACAT GGGTGCCCTC CACGTCCCTC ATATCCCCAG GCACACTCTG GCCTCAGGTT
61    TTGCCCTGGC CATGTCATCT ACCTGGAGTG GGCCCTCCCC TTCTTCAGCC TTGAATCAAA
121   AGCCACTTTG TTAGGCGAGG ATTTCCCAGA CCACTCATCA CATTAAAAAA TATTTTGAAA
181   ACAAAAAAAA AAAAAAA 55B (SEQ ID NO: 6)
1     TTGACAAAGC TGTTTATTTC CACCAATAAA TAGTATATGG TGATTGGGGT TTCTATTTAT
61    AAGAGTAGTG GCTATTATAT GGGGTATCAT GTTGATGCTC ATAAATAGTT CATATCTACT
121   TAATTTGCCT TC 60B (SEQ ID NO: 7)
1     GAAGAGAGTT GTATGTACAA CCCCAACAGG CAAGGCAGCT AAATGCAGAG GGTACAGAGA
61    GATCCCGAGG GAATT 86B (SEQ ID NO: 8)
1     GGATGGAAAC ATGTAGAAGT CCAGAGAAAA ACAATTTTAA AAAAAGGTGG AAAAGTTACG
61    GCAAACCTGA GATTTCAGCA TAAAATCTTT AGTTAGAAGT GAGAGAAAGA AGAGGAGGC
121   TGGTTGCTGT TGCACGTATC AATAGGTTAT C 87B (SEQ ID NO: 9)
1     TTCTTGATCT TTAGAACACT ATGAATAGGG AAAAAAGAAA AAACTGTTCA AAATAAAATG
61    TAGGAGCCGT GCTTTTGGAA TGCTTGAGTG AGGAGCTCAA CAAGTCCTCT CCCAAGAAAG
181   CAATGATAAA ACTTGACAAA A 98B (SEQ ID NO: 10)
1     ACCCATTTCT AACAATTTTT ACTGTAAAAT TTTTGGTCAA AGTTCTAAGC TTAATCACAT
61    CTCAAAGAAT AGAGGCAATA TATAGCCCAT CTTACTAGAC ATACAGTATT AAACTGGACT
121   GAATATGAGG ACAAGCTCTA GTGGTCATTA AACCCCTCAG AA 110B (SEQ ID NO: 11)
1     ACATATATTA ACAGCATTCA TTTGGCCAAA ATCTACACGT TTGTAGAATC CTACTGTATA
61    TAAAGTGGGA ATGTATCAAG TATAGACTAT GAAAGTGCAA ATAACAAGTC AAGGTTAGAT
121   TAACTTTTTT TTTTTACATT ATAAAATTAA CTTGTTT 118B (SEQ ID NO: 12)
1     CCAAATTTCT CTGGAATCCA TCCTCCCTCC CATCACCATA GCCTCGAGAC GTCATTTCTG
61    TTTGACTACT CCAGC 133B (SEQ ID NO: 13)
1     AACTAACCTC CTCGGACCCC TGCCTCACTC ATTTACACCA ACCACCCAAC TATCTATAAA
61    CCTGAGCCAT GGCCATCCCT TATGAGCGGC GCAGTGATTA TAGGCTTTCG CTCTAAGATA
121   AAAT 140B (SEQ ID NO: 14)
1     ATTATTATTC TTTTTTTATG TTAGCTTAGC CATGCAAAAT TTACTGGTGA AGCAGTTAAT
61    AAAACACACA TCCCATTGAA GGGTTTTGTA CATTTCAGTC CTTACAAATA ACAAAGCAAT
121   GATAAACCCG GCACGTCCTG ATAGGAAATT C 144B (SEQ ID NO: 15)
1     CGTGACACAA ACATGCATTC GTTTTATTCA TAAAACAGCC TGGTTTCCTA AAACAATACA
61    AACAGCATGT TCATCAGCAG GAAGCTGGCC GTGGGCAGGG GGGCC

198B[a] (SEQ ID NO: 16)
1     ATAGGTTAGA TTCTCATTCA CGGGACTAGT TAGCTTTAAG CACCCTAGAG GACTAGGGTA
61    ATCTGACTTC TCACTTCCTA AGTTCCCTCT TATATCCTCA AGGTAGAAAT GTCTATGTTT
121   TCTACTCCAA TTCATAAATC TATTCATAAG TCTTTGGTAC AAGTTACATG ATAAAAAGAA
181   ATGTGATTTG TCTTCCCTTC TTTGCACTTT TGAAATAAAG TATTTATCTC CTGTCTACAG
241   TTTAAT 212B (SEQ ID NO: 17)
1     GTCCAGTATA AAGGAAAGCG TTAAGTCGGT AAGCTAGAGG ATTGTAAATA TCTTTTATGT

TABLE I-continued

SEQUENCES OF 31 NOVEL OC-SPECIFIC OR -RELATED cDNA CLONES

```
 61    CCTCTAGATA AAACACCCGA TTAACAGATG TTAACCTTTT ATGTTTTGAT TTGCTTTAAA
121    AATGGCTTTC TACACATTAG CTCCAGCTAA AAAGACACAT TGAGAGCTTA GAGGATAGTC
181    TCTGGAGC

223B^b (SEQ ID NO: 18)
  1    GCACTTGGAA GGGAGTTGGT GTGCTATTTT TGAAGCAGAT GTGGTGATAC TGAGATTGTC
 61    TGTTCAGTTT CCCCATTTGT TTGTGCTTCA AATGATCCTT CCTACTTTGC TTCTCTCCAC
121    CCATGACCTT TTTCACTGTG GCCATCAAGG ACTTTCCTGA CAGCTTGTGT ACTCTTAGGC
181    TAAGAGATGT GACTACAGCC TGCCCCTGAC TG 241B (SEQ ID NO: 19)
  1    TGTTAGTTTT TAGGAAGGCC TGTCTTCTGG GAGTGAGGTT TATTAGTCCA CTTCTTGGAG
 61    CTAGACGTCC TATAGTTAGT CACTGGGGAT GGTGAAAGAG GGAGAAGAGG AAGGGCGAAG
121    GGAAGGGCTC TTTGCTAGTA TCTCCATTTC TAGAAGATGG TTTAGATGAT AACCACAGGT
181    CTATATGAGC ATAGTAAGGC TGT

32C^b (SEQ ID NO: 20)
  1    CCTATTTCTG ATCCTGACTT TGGACAAGGC CCTTCAGCCA GAAGACTGAC AAAGTCATCC
121    TCCGTCTACC AGAGCGTGCA CTTGTGATCC TAAAATAAGC TTCATCTCCG GCTGTGCCTT
161    GGGTGGAAGG GGCAGGATTC TGCAGCTGCT TTTGCATTTC TCTTCCTAAA TTTCATT 34C (SEQ ID NO: 21)
  1    CGGAGCGTAG GTGTGTTTAT TCCTGTACAA ATCATTACAA AACCAAGTCT GGGGCAGTCA
 61    CCGCCCCCAC CCATCACCCC AGTGCAATGG CTAGCTGCTG GCCTTT 47C (SEQ ID NO: 22)
  1    TTAGTTCAGT CAAAGCAGGC AACCCCCTTT GGCACTGCTG CCACTGGGGT CATGGCGGTT
 61    GTGGCAGCTG GGGAGGTTTC CCCAACACCC TCCTCTGCTT CCCTGTGTGT CGGGGTCTCA
121    GGAGCTGACC CAGAGTGGA 65C (SEQ ID NO: 23)
  1    GCTGAATGTT TAAGAGAGAT TTTGGTCTTA AAGGCTTCAT CATGAAAGTG TACATGCATA
 61    TGCAAGTGTG AATTACGTGG TATGGATGGT TGCTTGTTTA TTAACTAAAG ATGTACAGCA
121    AACTGCCCGT TTAGAGTCCT CTTAATATTG ATGTCCTAAC ACTGGGTCTG CTTATGC 79C (SEQ ID NO: 24)
  1    GGCAGTGGGA TATGGAATCC AGAAGGGAAA CAAGCACTGG ATAATTAAAA ACAGCTGGGG
 61    AGAAAACTGG GGAAACAAAG GATATATCCT CATGGCTCGA ATAAGAACA ACGCCTGTGG
121    CATTGCCAAC CTGGCCAGCT TCCCCAAGAT GTGACTCCAG CCAGAAA 84C (SEQ ID NO: 25)
  1    GCCAGGGCGG ACCGTCTTTA TTCCTCTCCT GCCTCAGAGG TCAGGAAGGA GGTCTGGCAG
 61    GACCTGCAGT GGGCCCTAGT CATCTGTGGC AGCGAAGGTG AAGGGACTCA CCTTGTCGCC
121    CGTGCCTGAG TAGAACTTGT TCTGGAATTC C 86C (SEQ ID NO: 26)
  1    AACTCTTTCA CACTCTGGTA TTTTTAGTTT AACAATATAT GTGTTGTGTC TTGGAAATTA
 61    GTTCATATCA ATTCATATTG AGCTGTCTCA TTCTTTTTTT AATGGTCATA TACAGTAGTA
121    TTCAATTATA AGAATATATC CTAATACTTT TTAAAA 87C (SEQ ID NO: 27)
  1    GGATAAGAAA GAAGGCCTGA GGGCTAGGGG CCGGGGCTGG CCTGCGTCTC AGTCCTGGGA
 61    CGCAGCAGCC CGCACAGGTT GAGAGGGGCA CTTCCTCTTG CTTAGGTTGG TGAGGATCTG
121    GTCCTGGTTG GCCGGTGGAG AGCCACAAAA 88C (SEQ ID NO: 28)
  1    CTGACCTTCG AGAGTTTGAC CTGGAGCCGG ATACCTACTG CCGCTATGAC TCGGTCAGCG
 61    TGTTCAACGG AGCCGTGAGC GACGACTCCG GTGGGGAAGT TCTGCGGCGA T 89C (SEQ ID NO: 29)
  1    ATCCCTGGCT GTGGATAGTG CTTTTGTGTA GCAAATGCTC CCTCCTTAAG GTTATAGGGC
 61    TCCCTGAGTT TGGGAGTGTG GAAGTACTAC TTAACTGTCT GTCCTGCTTG GCTGTCGTTA
121    TCGTTTTCTG GTGATGTTGT GCTAACAATA AGAATAC 101C (SEQ ID NO: 30)
  1    GGCTGGGCAT CCCTCTCCTC CTCCATCCCC ATACATCACC AGGTCTAATG TTTACAAACG
 61    GTGCCAGCCC GGCTCTGAAG CCAAGGGCCG TCCGTGCCAC GGTGGCTGTG AGTATTCCTC
121    CGTTAGCTTT CCCATAAGGT TGGAGTATCT GC 112C (SEQ ID NO: 31)
  1    CCAACTCCTA CCGCGATACA GACCCACAGA GTGCCATCCC TGAGAGACCA GACCGCTCCC
161    CAATACTCTC CTAAAATAAA CATGAAGCAC
```

TABLE I-continued

SEQUENCES OF 31 NOVEL OC-SPECIFIC OR -RELATED cDNA CLONES 114C (SEQ ID NO: 32)
1     CATGGATGAA TGTCTCATGG TGGGAAGGAA CATGGTACAT TTC

[a]Repeated 3 times
[b]Repeated 2 times

Sequence analysis of the $OC^+$ stromal $cell^-$ cloned DNA sequences revealed, in addition to the novel sequences, a number of previously-described genes. The known genes identified (including type 5 acid phosphatase, gelatinase B, cystatin C (13 clones), Alu repeat sequences (11 clones), creatnine kinase (6 clones) and others) are summarized in Table II. In situ hybridization (described below) directly demonstrated that gelatinase B mRNA is expressed in multi-nucleated osteoclasts and not in stromal cells. Although gelatinase B is a well-characterized protease, its expression at high levels in osteoclasts has not been previously described. Taken together, these results demonstrate that the identified DNA sequences are osteoclast-expressed, thereby confirming the effectiveness of the differential screening strategy for identifying osteoclast-specific or -related DNA sequences. Therefore, novel genes comprising DNA sequences identified by this method have a high probability of being OC-specific or -related.

In addition, a minority of the genes identified by this screen are probably not expressed by OCs (Table II) based on external considerations. For example, type III collagen (6 clones), collagen type I (1 clone), dermatansulfate (1 clone), and type VI collagen (1 clone) probably originate from the stromal cells or from osteoblastic cells which are present in the tumor. These cDNA sequences survive the differential screening process either because the cells which produce them in the tumor in vivo die out during the stromal cell propagation phase, or because they stop producing their product in vitro. These clones do not constitute more than 5–10% of the all sequences selected by differential hybridization.

TABLE II

SEQUENCE ANALYSIS OF CLONES CONTAINING KNOWN SEQUENCES FROM AN OSTEOCLASTOMA cDNA LIBRARY

| | |
|---|---|
| Clones with Sequence Homology to Collagenase Type IV | 25 total |
| Clones with Sequence Homology to Type 5 Tartrate Resistant Acid Phosphatase | 14 total |
| Clones with Sequence Homology to Cystatin C | 13 total |
| Clones with Sequence Homology to Alu-repeat Sequences | 11 total |
| Clones with Sequence Homology to Creatnine Kinase | 6 total |
| Clones with Sequence Homology to Type III Collagen | 6 total |
| Clones with Sequence Homology to MHC Class I γ Invariant Chain | 5 total |
| Clones with Sequence Homology to MHC Class II β Chain | 3 total |
| One or Two Clone(s) with Sequence Homology to Each of the Following: | 10 total |
| αI collagen type I | |
| γ interferon inducible protein | |
| osteopontin | |
| Human chondroitin/dermatansulfate | |
| α globin | |

TABLE II-continued

SEQUENCE ANALYSIS OF CLONES CONTAINING KNOWN SEQUENCES FROM AN OSTEOCLASTOMA cDNA LIBRARY

β glucosidase/sphingolipid activator
Human CAPL protein (Ca binding)
Human EST 01024
Type VI collagen
Human EST 00553

EXAMPLE 5

In situ Hybridization of OC-Expressed Genes

In situ hybridization was performed using probes derived from novel cloned sequences in order to determine whether the novel putative OC-specific or -related sequences are differentially expressed in osteoclasts (and not expressed in the stromal cells) of human giant cell tumors. Initially, in situ hybridization was performed using antisense (positive) and sense (negative control) cRNA probes against human type IV collagenase/gelatinase B labelled with $^{35}$S-UTP.

A thin section of human giant cell tumor reacted with the antisense probe resulted in intense labelling of all OCs, as indicated by the deposition of silver grains over these cells, but failed to label the stromal cell elements. In contrast, only minimal background labelling was observed with the sense (negative control) probe. this result confirmed that gelatinase B is expressed in human OCs.

In situ hybridization was then carried out using cRNA probes derived from 11 of the 31 novel genes, labelled with digoxigenin UTP according to known methods.

The results of this analysis are summarized in Table III. Clones 28B, 118B, 140B, 198B, and 212B all gave positive reactions with OCs in frozen sections of a giant cell tumor, as did the positive control gelatinase B. 198B is repeated three times, indicating relatively high expression. Clones 4B, 37B, 88C and 98B produced positive reactions with the tumor tissue; however the signal was not well-localized to OCs. Clones 86B and 87B failed to give a positive reaction with any cell type, possibly indicating very low level expression which makes these sequences difficult to study further.

To generate probes for the in situ hybridizations, cDNA derived from novel cloned osteoclast-specific or -related cDNA was subcloned into a BlueScript II SK(−) vector. The orientation of cloned inserts was determined by restriction analysis of subclones. The T7 and T3 promoters in the BlueScriptII vector was used to generate $^{35}$S-labelled ($^{35}$S-UTP, 850 Ci/mmol, Amersham, Arlington Heights, Ill.), or UTP digoxygenin labelled cRNA probes.

TABLE III

In Situ HYBRIDIZATION USING PROBES
DERIVED FROM NOVEL SEQUENCES

| | Reactivity with: | |
|---|---|---|
| Clone | Osteoclasts | Stromal Cells |
| 4B | + | + |
| 28B | + | − |
| 37B | + | + |
| 86B | − | − |
| 87B | − | − |
| 88C | + | + |
| 98B | + | + |
| 118B | + | − |
| 140B | + | − |
| 198B | + | − |
| 212B | + | − |
| Gelatinase B | + | − |

In situ hybridization was carried out on 7 micron cryostat sections of a human osteoclastoma as described previously (Chang, L. C. et al. *Cancer Res.* 49:6700 (1989)). Briefly, tissue was fixed in 4% paraformaldehyde and embedded in OCT (Miles Inc., Kankakee, Ill.). The sections were rehydrated, postfixed in 4% paraformaldehyde, washed, and pretreated with 10 mM DTT, 10 mM iodoacetamide, 10 mM N-ethylmaleimide and 0.1 triethanolamine-HCL. Prehybridization was done with 50% deionized formamide, 10 mM Tris-HCl, pH 7.0, 1×Denhardt's, 500 mg/ml tRNA, 80 mg/ml salmon sperm DNA, 0.3 M NaCl, 1 mM EDTA, and 100 mM DTT at 45° C. for 2 hours. Fresh hybridization solution containing 10% dextran sulfate and 1.5 ng/ml $^{35}$S-labelled or digoxygenin labelled RNA probe was applied after heat denaturation. Sections were coverslipped and then incubated in a moistened chamber at 45–50° C. overnight. Hybridized sections were washed four times with 50% formamide, 2×SSC, containing 10 mM DTT and 0.5% Triton X-100 at 45° C. Sections were treated with RNase A and RNase T1 to digest single-stranded RNA, washed four times in 2×SSC/10 mM DTT.

In order to detect $^{35}$S-labelling by autoradiography, slides were dehydrated, dried, and coated with Kodak NTB-2 emulsion. The duplicate slides were split, and each set was placed in a black box with desiccant, sealed, and incubated at 4° C. for 2 days. The slides were developed (4 minutes) and fixed (5 minutes) using Kodak developer D19 and Kodak fixer. Hematoxylin and eosin were used as counterstains.

In order to detect digoxygenin-labelled probes, a Nucleic Acid Detection Kit (Boehringer-Mannheim, Cat. # 1175041) was used. Slides were washed in Buffer 1 consisting of 100 mM Tris/150 mM NaCl, pH7.5, for 1 minute. 100 µl Buffer 2 was added (made by adding 2 mg/ml blocking reagent as provided by the manufacturer) in Buffer 1 to each slide. The slides were placed on a shaker and gently swirled at 20° C.

Antibody solutions were diluted 1:100 with Buffer 2 (as provided by the manufacturer). 100 µl of diluted antibody solution was applied to the slides and the slides were then incubated in a chamber for 1 hour at room temperature. The slides were monitored to avoid drying. After incubation with antibody solution, slides were washed in Buffer 1 for 10 minutes, then washed in Buffer 3 containing 2 mM levamisole for 2 minutes.

After washing, 100 µl color solution was added to the slides. Color solution consisted of nitroblue/tetrazolium salt (NBT) (1:225 dilution) 4.5 µl, 5-bromo-4-chloro-3-indolyl phosphate (1:285 dilution) 3.5 µl, levamisole 0.2 mg in Buffer 3 (as provided by the manufacturer) in a total volume of 1 ml. Color solution was prepared immediately before use.

After adding the color solution, the slides were placed in a dark, humidified chamber at 20° C. for 2–5 hours and monitored for color development. The color reaction was stopped by rinsing slides in TE Buffer.

The slides were stained for 60 seconds in 0.25% methyl green, washed with tap water, then mounted with water-based Permount (Fisher).

EXAMPLE 6

Immunohistochemistry

Immunohistochemical staining was performed on frozen and paraffin embedded tissues as well as on cytospin preparations (see Table IV). The following antibodies were used: polyclonal rabbit anti-human gelatinase antibodies; Ab110 for gelatinase B; monoclonal mouse anti-human CD68 antibody (clone KP1) (DAKO, Denmark); Mo1 (anti-CD11b) and Mo2 (anti-CD14) derived from ATCC cell lines HB CRL 8026 and TIB 228/ HB44. The anti-human gelatinase B antibody Ab110 was raised against a synthetic peptide with the amino acid sequence EALMYPMYRFTEGPPLHK (SEQ ID NO: 34), which is specific for human gelatinase B (Corcoran, M. L. et al. *J. Biol. Chem.* 267:515 (1992)).

Detection of the immunohistochemical staining was achieved by using a goat anti-rabbit glucose oxidase kit (Vector Laboratories, Burlingame Calif.) according to the manufacturer's directions. Briefly, the sections were rehydrated and pretested with either acetone or 0.1% trypsin. Normal goat serum was used to block nonspecific binding. Incubation with the primary antibody for 2 hours or overnight (Ab110: 1/500 dilution) was followed by either a glucose oxidase labeled secondary anti-rabbit serum, or, in the case of the mouse monoclonal antibodies, were reacted with purified rabbit anti-mouse Ig before incubation with the secondary antibody.

Paraffin embedded and frozen sections from osteoclastomas (GCT) were reacted with a rabbit antiserum against gelatinase B (antibody 110) (Corcoran, M. L. et al. *J. Biol. Chem.* 267:515 (1992)), followed by color development with glucose oxidase linked reagents. The osteoclasts of a giant cell tumor were uniformly strongly positive for gelatinase B, whereas the stromal cells were unreactive. Control sections reacted with rabbit preimmune serum were negative. Identical findings were obtained for all 8 long bone giant cell tumors tested (Table IV). The osteoclasts present in three out of four central giant cell granulomas (GCG) of the mandible were also positive for gelatinase B expression. These neoplasms are similar but not identical to the long bone giant cell tumors, apart from their location in the jaws (Shafer, W. G. et al., Textbook of Oral Pathology, W. B. Saunders Company, Philadelphia, pp. 144–149 (1983)). In contrast, the multinucleated cells from a peripheral giant cell tumor, which is a generally non-resorptive tumor of oral soft tissue, were unreactive with antibody 110 (Shafer, W. G. et al., Textbook of Oral Pathology, W. B. Saunders Company, Philadelphia, pp. 144–149 (1983)).

Antibody 110 was also utilized to assess the presence of gelatinase B in normal bone (n=3) and in Paget's disease, in which there is elevated bone remodeling and increased osteoclastic activity. Strong staining for gelatinase B was observed in osteoclasts both in normal bone (mandible of a 2 year old), and in Paget's disease. Staining was again absent in controls incubated with preimmune serum. Osteoblasts did not stain in any of the tissue sections, indicating that gelatinase B expression is limited to osteoclasts in bone. Finally, peripheral blood monocytes were also reactive with antibody 110 (Table IV).

TABLE IV

DISTRIBUTION OF GELATINASE B IN VARIOUS TISSUES

| Samples | Antibodies tested Ab 110 gelatinase B |
|---|---|
| GCT frozen (n = 2) | |
| giant cells | + |
| stromal cells | − |
| GCT paraffin (n = 6) | |
| giant cells | + |
| stromal cells | − |
| central GCG (n = 4) | |
| giant cells | + (¾) |
| stromal cells | − |
| peripheral GCT (n-4) | |
| giant cells | − |
| stromal cells | − |
| Paget's disease (n = 1) | |
| osteoclasts | + |
| osteoblasts | − |
| normal bone (n = 3) | |
| osteoclasts | + |
| osteoblasts | − |
| monocytes (cytospin) | + |

Distribution of gelatinase B in multinucleated giant cells, osteoclasts, osteoblasts and stromal cells in various tissues. In general, paraffin embedded tissues were used for these experiments; exceptions are indicated.

EXAMPLE 7

Identification of Cathepsin X

For full-length cDNA characterization, a cathepsin X probe, i.e., a cDNA that hybridized with clones derived from the osteoclastoma tumor but not with clones derived from stromal cells, was labeled with $\alpha[^{32}P]dCTP$ used to screen the Lambda-ZAP osteoclastoma library. Positive clones were purified, and the size of inserts was determined following excision with EcoRI. A clone containing a full-length insert of 1.6 kb was subjected to controlled digestion with ExoIII to generate a series of diminishing insert sizes. Sequence analysis was then carried out on both ends by the dideoxy method. Homologies with known cathepsin sequences were determined using the BLAST program at N.C.B.I.

For in situ hybridization, the 0.8 kb cathepsin X insert was subcloned into pBluescript SK, and cRNA probes were generated from the T3 (sense) and T7 (antisense) promoters, respectively. Probes were labeled with digoxygenin-UTP using the Genius System (Boehringer, Indianapolis, Ind.). In situ hybridization was carried out on 7 µm cryostat sections of a human osteoclastoma as described previously (Wucherpfennig, A. L. et al., *J. Bone Miner Res.*, 9:549–556 (1994)). In brief, tissue was fixed with 4% paraformaldehyde and embedded in OCT (Miles, Inc., Kankakee, Ill.). The sections were rehydrated, postfixed in 4% paraformaldehyde, washed, and pretreated with 10 mM dithiothreitol, 10 mM iodo-acetamide, 10 mM N-ethylmaleimide, and 0.1% thiethanolamine-HCl. Prehybridization was carried out with 50% deionized formamide, 10 mM Tris-HCl, pH 7.0, Denhardt's 500 µg/ml of yeast tRNA, 80 µg/ml of salmon sperm DNA, 0.3M NaCl, 1 mM EDTA, an 100 mM DTT at 45° C. for 2 h. Fresh hybridization solution containing 10% dextran sulfate and 1.5 ng/ml of digoxygenin-labeled cRNA probe was applied after heat denaturation. Sections were coverslipped and incubated in a moistened chamber at 45–50° C. overnight. Hybridized sections were washed four times with 50% formamide and 2×SC (0.3 M NaCl, 30 mM sodium citrate, pH 7.0) containing 10 mM DTT and 0.5% Triton X-100 at 45° C. Sections were treated with RNAse A and RNAse T1 to digest single-stranded RNA and washed four times in 2×SSC and 10 mM DTT. Hybridized probes were visualized immunologically with a digoxygenin-nucleic acid detection kit according to the manufacturer's instructions (Genius System, Boehringer Mannheim). Developed slides were photographed using a Nikon Diaphot microscope. Hybridized probes were visualized immunologically with a digoxygenin-nucleic acid detection kit according to the manufacturer's instructions. Developed slides were photographed using a Nikon Diaphot microscope.

The complete nucleotide and deduced amino acid sequences of cathepsin X are presented in FIG. 2. An open reading frame of 987 bp originating with ATG was identified. This was preceded by an 18 bp portion of the 5' untranslated region and poly(A18) for a total insert size of 1615 bp. Database searches revealed 92% homology at the nucleotide level within the coding region to a recently described cysteine proteinase termed OC-2 cloned in the rabbit (Tezuka, K. et al., *J. Bio. Chem.*, 269:1106–1109 (1994)). Limited homology was observed with OC-2 in the 3' untranslated region, as expected for genes from different species. Lesser degrees of homology to human cathepsin L (64%), S (63%), and B (45%) were also observed. A high degree of homology was observed with rabbit OC-2 (93.9%), with many of the differences reflecting conservative amino acid substitutions. Considerably less homology was seen with cathepsins L (46.9%) and S (52.2%). The sequence of cathepsin X was submitted to GenBank (accession number U20280).

EXAMPLE 8

Identification of Proton Pump Gene

For full-length cDNA characterization, a 1.0 kb putative proton pump probe, i.e., a cDNA that hybridized with clones derived from the osteoclastoma tumor but not with clones derived from stromal cells, labelled with $\alpha^{32}PdCTP$ was used to screen the Lambda-ZAP osteoclastoma library. Positive clones were purified, and the size of inserts was determined following excision with Kpn1 and Xbal. A clone containing a full-length insert of 2.6 kb was subjected to controlled digestion with ExoIII to generate a series of diminishing insert sizes. Sequence analysis was then carried out from both ends by the dideoxy method (Sanger et al., *Proc. Natl. Acad. Sci. USA*, 74: 5463–5467 (1977)) using the Sequenase kit (U.S. Biochemical Corp). Homologies were compared with known proton pump sequences using the BLAST program at the National Center for Biotechnology Information (N.C.B.I.).

Total RNA from osteoclastomas and cell lines was isolated by the method of Chomczynski and Sacchi (Chomczynski and Sacchi, *Analytical Biochemistry*, 162(1):156–159 (1987)). Whole cell RNA from human tissues was purchased from Clontech, Palto Alto, Calif. Total cellular RNA was separated on a 1.0% agarose gel containing 6% formamide and transferred to nylon membranes. The integrity and quality of RNA was confirmed by ethidium bromide staining. Both 1.0 kb 3'-end and 0.5 kb 5'-end OC-116KDa cDNAs were used as probes. Probes were radiolabeled with $\alpha^{32}$pdCTP using a random primer labeling kit (Stratagene). Hybridization was performed as described previously in Li et al. (1995).

In situ hybridization was performed as described in Li et al. (1995). Briefly, the 1.0 kb OC-116KDa insert was subcloned into pBluescript SK, and cDNA probes were generated from the T3 (sense) and T7 (antisense) promoters respectively. Probes were labelled with digoxygenin-UTP using the Genius System (Boehringer Mannheim) and developed with an alkaline phosphatase-labelled antibody. In situ hybridization was carried out on 7 mm cryostat sections of a human osteoclastoma. Hybridized probes were visualized immunologically with a digoxygenin-nucleic acid detection kit according to the manufacturer's instructions (Genius System, Boehringer Mannheim). Developed slides were photographed using a Nikon Diaphot microscope.

The nucleotide sequence (SEQ ID NO: 37) and the deduced amino acid sequence (SEQ ID NO: 38) of the OC-116KDa cDNA clone are shown in FIGS. 3A and 3E. The nucleotide sequence of the cDNA encoding the OC-116KDa proton pump polypeptide contains 2622 base pairs excluding the 3'-poly(A) tail. The cDNA contains a 57 base pair 5' untranslated region, and a rather short 3' untranslated region of 99 base pairs. The nucleotide sequence contains an open reading frame, starting from the first ATG codon, encoding an 822-amino acid polypeptide. The sequence context of the putative initiator methionine has a flanking sequence in agreement with the consensus sequences for an initiator methionine (1/G)CCATGG) (Kozak, *Nucleic Acids Res.*, 15:8125–8148 (1987)). At the 3' end, the AATAAA sequence is a common polyadenylation signal. The cDNA is full-length as judged by the fact that its size corresponds well to the message size observed on RNA blots and that it contains an in-frame termination codon 5' to the initiator methionine. In addition, the cDNA sequence exhibits a single large open reading frame, the translation of which predicts the synthesis of an 822-amino acid protein.

Database searches revealed that OC-116KDa shows 59.4% homology at the nucleotide level with the rat 116-kDa subunit of the clathrin-coated vesicle proton pump and 59.1% homology with the bovine brain 116-kDa subunit vacuolar proton pump. OC-116KDa exhibits 46.9; and 47.2% homology at the amino acid level with the rat 116KDa polypeptide and the bovine 116KDa polypeptide, respectively (Perin et al., *J. Biol. Chem.* 266:3877–3881 (1991); Peng et al., *J. Biol. Chem.* 269:17262–17266 (1994)).

The composition of OC-116KDa is characterized by an abundance of hydrophilic resides in the first 390 amino acids and a rather hydrophobic region in the following 432 amino acids. Hydrophobicity plots indicate that at least six transmembrane regions are present in the carboxyl-terminal portion of the molecule. The putative transmembrane regions are separated by spacer regions of different length and hydrophilicity (data not shown).

Based on the hydropathy plots, OC-116KDa shows structural homology with other 116KDa hydrophobic membrane proteins with transport-related function, including rat- and bovine-116KDa (Perin et al. (1991)). All three proteins are about 830 amino acids in length and contain six transmembrane domains with a hydrophilic region between domains.

Cells within the osteoclastoma tumor which produce mRNA for OC-116KDa were identified by in situ hybridization. A digoxygenin-labelled antisense probe was strongly reactive with all multinucleated osteoclasts, but was unreactive with stromal cells. In contrast, the sense probe produced only minimal background staining, which was not localized to any cell type.

EQUIVALENTS

Those skilled in the art will recognize, or be able to ascertain using no more than routine experimentation, many equivalents to the specific embodiments described herein. Such equivalents are intended to be encompassed by the following claims:

What is claimed is:

1. An isolated osteoclast-specific or -related DNA sequence selected from the group consisting of:
   a) DNA sehquences of SEQ ID NOs: 7, 8, 9, 18, 24 and 25; and
   b) the full complements of SEQ ID NOs: 7, 8, 9, 18, 24 and 25.

2. A DNA construct capable of replicating, in a host cell, osteoclast-specific or -related DNA, said construct comprising:
   a) a DNA sequence selected from the group consisting of:
      i. SEQ ID NOs: 7, 8, 9, 18, 24, and 25; and
      ii. the full complements of SEQ ID NOs: 7, 8, 9, 18, 24, and 25; and
   b) at least one regulatory sequence operably linked to said DNA sequence, wherein said regulatory sequence is necessary for transforming or transfecting a host cell, and for replicating, said DNA sequence.

3. An expression vector capable of replicating and expressing, in a host cell, an osteoclast-specific or -related DNA, said construct comprising:
   a) a DNA sequence selected from the group consisting of:
      i. SEQ ID NOs: 7, 8, 9, 18, 24, and 25; and
      ii. the full complements of SEQ ID NOs: 7, 8, 9, 18, 24, and 25; and
   b) at least one regulatory sequence operably linked to said DNA sequence, wherein said regulatory sequence is necessary for transforming or transfecting a host cell, and for directing the expression of said DNA sequence.

4. A cell stably transformed or transfected with a DNA construct comprising:
   a) a DNA sequence selected from the group consisting of:
      i. SEQ ID NOs: 7, 8, 9, 18, 24, and 25; and
      ii. the full complements of SEQ ID NOs: 7, 8, 9, 18, 24, and 25; and
   b) at least one regulatory sequence, in addition to said DNA sequence, wherein said regulatory sequence is necessary for transforming or transfecting a host cell, and for replicating, said DNA sequence.

5. A cell stably transformed or transfected with an expression vector comprising:
   a) a DNA sequence selected from the group consisting of:
      i. SEQ ID NOs: 7, 8, 9, 18, 24, and 25; and
      ii. the full complements of SEQ ID NOs: 7, 8, 9, 18, 24, and 25; and
   b) at least one regulatory sequence operably linked to said DNA sequence, wherein said regulatory sequence is necessary for transforming or transfecting a host cell, and for directing the expression of said DNA sequence.

* * * * *

SEQUENCE LISTING (1) GENERAL INFORMATION:

(iii) NUMBER OF SEQUENCES: 38

(2) INFORMATION FOR SEQ ID NO:1:

(i) SEQUENCE CHARACTERISTICS:
        (A) LENGTH: 170 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

```
GCAAATATCT AAGTTTATTG CTTGGATTTC TAGTGAGAGC TGTTGAATTT GGTGATGTCA      60

AATGTTTCTA GGGTTTTTTT AGTTTGTTTT TATTGAAAAA TTTAATTATT TATGCTATAG     120

GTGATATTCT CTTTGAATAA ACCTATAATA GAAAATAGCA GCAGACAACA                170
```

(2) INFORMATION FOR SEQ ID NO:2:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

```
GTGTCAACCT GCATATCCTA AAAATGTCAA AATGCTGCAT CTGGTTAATG TCGGGGTAGG      60

GGG                                                                    63
```

(2) INFORMATION FOR SEQ ID NO:3:

(i) SEQUENCE CHARACTERISTICS:
        (A) LENGTH: 163 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
CTTCCCTCTC TTGCTTCCCT TTCCCAAGCA GAGGTGCTCA CTCCATGGCC ACCGCCACCA      60

CAGGCCCACA GGGAGTACTG CCAGACTACT GCTGATGTTC TCTTAAGGCC CAGGGAGTCT     120

CAACCAGCTG GTGGTGAATG CTGCCTGGCA CGGGACCCCC CCC                       163
```

(2) INFORMATION FOR SEQ ID NO:4:

(i) SEQUENCE CHARACTERISTICS:
        (A) LENGTH: 173 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
TTTTATTTGT AAATATATGT ATTACATCCC TAGAAAAAGA ATCCCAGGAT TTTCCCTCCT      60

GTGTGTTTTC GTCTTGCTTC TTCATGGTCC ATGATGCCAG CTGAGGTTGT CAGTACAATG     120

AAACCAAACT GGCGGGATGG AAGCAGATTA TTCTGCCATT TTTCCAGGTC TTT            173
```

(2) INFORMATION FOR SEQ ID NO:5:

(i) SEQUENCE CHARACTERISTICS:
        (A) LENGTH: 197 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
GGCTGGACAT GGGTGCCCTC CACGTCCCTC ATATCCCCAG GCACACTCTG GCCTCAGGTT      60

TTGCCCTGGC CATGTCATCT ACCTGGAGTG GGCCCTCCCC TTCTTCAGCC TTGAATCAAA     120

AGCCACTTTG TTAGGCGAGG ATTTCCCAGA CCACTCATCA CATTAAAAAA TATTTTGAAA     180

ACAAAAAAAA AAAAAA                                                     197
```

(2) INFORMATION FOR SEQ ID NO:6:

(i) SEQUENCE CHARACTERISTICS:
    (A) LENGTH: 132 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:6:

```
TTGACAAAGC TGTTTATTTC CACCAATAAA TAGTATATGG TGATTGGGGT TTCTATTTAT     60
AAGAGTAGTG GCTATTATAT GGGGTATCAT GTTGATGCTC ATAAATAGTT CATATCTACT    120
TAATTTGCCT TC                                                        132
```

(2) INFORMATION FOR SEQ ID NO:7:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
GAAGAGAGTT GTATGTACAA CCCCAACAGG CAAGGCAGCT AAATGCAGAG GGTACAGAGA     60
GATCCCGAGG GAATT                                                     75
```

(2) INFORMATION FOR SEQ ID NO:8:

(i) SEQUENCE CHARACTERISTICS:
        (A) LENGTH: 151 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
GGATGGAAAC ATGTAGAAGT CCAGAGAAAA ACAATTTTAA AAAAAGGTGG AAAAGTTACG     60
GCAAACCTGA GATTTCAGCA TAAAATCTTT AGTTAGAAGT GAGAGAAAGA AGAGGGAGGC    120
TGGTTGCTGT TGCACGTATC AATAGGTTAT C                                   151
```

(2) INFORMATION FOR SEQ ID NO:9:

(i) SEQUENCE CHARACTERISTICS:
        (A) LENGTH: 141 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
TTCTTGATCT TTAGAACACT ATGAATAGGG AAAAAAGAAA AAACTGTTCA AAATAAAATG     60
TAGGAGCCGT GCTTTTGGAA TGCTTGAGTG AGGAGCTCAA CAAGTCCTCT CCCAAGAAAG    120
CAATGATAAA ACTTGACAAA A                                              141
```

(2) INFORMATION FOR SEQ ID NO:10:

(i) SEQUENCE CHARACTERISTICS:
        (A) LENGTH: 162 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO:10:

| | |
|---|---|
| ACCCATTTCT AACAATTTTT ACTGTAAAAT TTTTGGTCAA AGTTCTAAGC TTAATCACAT | 60 |
| CTCAAAGAAT AGAGGCAATA TATAGCCCAT CTTACTAGAC ATACAGTATT AAACTGGACT | 120 |
| GAATATGAGG ACAAGCTCTA GTGGTCATTA AACCCCTCAG AA | 162 |

(2) INFORMATION FOR SEQ ID NO:11:

(i) SEQUENCE CHARACTERISTICS:
        (A) LENGTH: 157 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

| | |
|---|---|
| ACATATATTA ACAGCATTCA TTTGGCCAAA ATCTACACGT TTGTAGAATC CTACTGTATA | 60 |
| TAAAGTGGGA ATGTATCAAG TATAGACTAT GAAAGTGCAA ATAACAAGTC AAGGTTAGAT | 120 |
| TAACTTTTTT TTTTTACATT ATAAAATTAA CTTGTTT | 157 |

(2) INFORMATION FOR SEQ ID NO:12:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

| | |
|---|---|
| CCAAATTTCT CTGGAATCCA TCCTCCCTCC CATCACCATA GCCTCGAGAC GTCATTTCTG | 60 |
| TTTGACTACT CCAGC | 75 |

(2) INFORMATION FOR SEQ ID NO:13:

(i) SEQUENCE CHARACTERISTICS:
        (A) LENGTH: 124 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

| | |
|---|---|
| AACTAACCTC CTCGGACCCC TGCCTCACTC ATTTACACCA ACCACCCAAC TATCTATAAA | 60 |
| CCTGAGCCAT GGCCATCCCT TATGAGCGGC GCAGTGATTA TAGGCTTTCG CTCTAAGATA | 120 |
| AAAT | 124 |

(2) INFORMATION FOR SEQ ID NO:14:

(i) SEQUENCE CHARACTERISTICS:
        (A) LENGTH: 151 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

```
ATTATTATTC TTTTTTTATG TTAGCTTAGC CATGCAAAAT TTACTGGTGA AGCAGTTAAT      60

AAAACACACA TCCCATTGAA GGGTTTTGTA CATTTCAGTC CTTACAAATA ACAAAGCAAT     120

GATAAACCCG GCACGTCCTG ATAGGAAATT C                                   151
```

(2) INFORMATION FOR SEQ ID NO:15:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

```
CGTGACACAA ACATGCATTC GTTTTATTCA TAAAACAGCC TGGTTTCCTA AAACAATACA      60

AACAGCATGT TCATCAGCAG GAAGCTGGCC GTGGGCAGGG GGGCC                    105
```

(2) INFORMATION FOR SEQ ID NO:16:

(i) SEQUENCE CHARACTERISTICS:
        (A) LENGTH: 246 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

```
ATAGGTTAGA TTCTCATTCA CGGGACTAGT TAGCTTTAAG CACCCTAGAG GACTAGGGTA      60

ATCTGACTTC TCACTTCCTA AGTTCCCTCT TATATCCTCA AGGTAGAAAT GTCTATGTTT     120

TCTACTCCAA TTCATAAATC TATTCATAAG TCTTTGGTAC AAGTTACATG ATAAAAGAA      180

ATGTGATTTG TCTTCCCTTC TTTGCACTTT TGAAATAAAG TATTTATCTC CTGTCTACAG     240

TTTAAT                                                               246
```

(2) INFORMATION FOR SEQ ID NO:17:

(i) SEQUENCE CHARACTERISTICS:
        (A) LENGTH: 188 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

```
GTCCAGTATA AAGGAAAGCG TTAAGTCGGT AAGCTAGAGG ATTGTAAATA TCTTTTATGT      60

CCTCTAGATA AAACACCCGA TTAACAGATG TTAACCTTTT ATGTTTTGAT TTGCTTTAAA     120

AATGGCCTTC TACACATTAG CTCCAGCTAA AAAGACACAT TGAGAGCTTA GAGGATAGTC     180

TCTGGAGC                                                             188
```

(2) INFORMATION FOR SEQ ID NO:18:

(i) SEQUENCE CHARACTERISTICS:
        (A) LENGTH: 212 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

```
GCACTTGGAA GGGAGTTGGT GTGCTATTTT TGAAGCAGAT GTGGTGATAC TGAGATTGTC      60
TGTTCAGTTT CCCCATTTGT TTGTGCTTCA AATGATCCTT CCTACTTTGC TTCTCTCCAC     120
CCATGACCTT TTTCACTGTG GCCATCAAGG ACTTTCCTGA CAGCTTGTGT ACTCTTAGGC     180
TAAGAGATGT GACTACAGCC TGCCCCTGAC TG                                   212
```

(2) INFORMATION FOR SEQ ID NO:19:

(i) SEQUENCE CHARACTERISTICS:
        (A) LENGTH: 203 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

```
TGTTAGTTTT TAGGAAGGCC TGTCTTCTGG GAGTGAGGTT TATTAGTCCA CTTCTTGGAG      60
CTAGACGTCC TATAGTTAGT CACTGGGGAT GGTGAAAGAG GGAGAAGAGG AAGGGCGAAG     120
GGAAGGGCTC TTTGCTAGTA TCTCCATTTC TAGAAGATGG TTTAGATGAT AACCACAGGT     180
CTATATGAGC ATAGTAAGGC TGT                                             203
```

(2) INFORMATION FOR SEQ ID NO:20:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

```
CCTATTTCTG ATCCTGACTT TGGACAAGGC CCTTCAGCCA GAAGACTGAC AAAGTCATCC      60
TCCGTCTACC AGAGCGTGCA CTTGTGATCC TAAAATAAGC TTCATCTCCG GCTGTGCCTT     120
GGGTGGAAGG GGCAGGATTC TGCAGCTGCT TTTGCATTTC TCTTCCTAAA TTTCATT        177
```

(2) INFORMATION FOR SEQ ID NO:21:

(i) SEQUENCE CHARACTERISTICS:
        (A) LENGTH: 106 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

```
CGGAGCGTAG GTGTGTTTAT TCCTGTACAA ATCATTACAA AACCAAGTCT GGGGCAGTCA      60
CCGCCCCCAC CCATCACCCC AGTGCAATGG CTAGCTGCTG GCCTTT                    106
```

(2) INFORMATION FOR SEQ ID NO:22:

(i) SEQUENCE CHARACTERISTICS:
        (A) LENGTH: 139 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

TTAGTTCAGT CAAAGCAGGC AACCCCCTTT GGCACTGCTG CCACTGGGGT CATGGCGGTT      60

GTGGCAGCTG GGGAGGTTTC CCCAACACCC TCCTCTGCTT CCCTGTGTGT CGGGGTCTCA     120

GGAGCTGACC CAGAGTGGA                                                 139

(2) INFORMATION FOR SEQ ID NO:23:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

GCTGAATGTT TAAGAGAGAT TTTGGTCTTA AAGGCTTCAT CATGAAAGTG TACATGCATA      60

TGCAAGTGTG AATTACGTGG TATGGATGGT TGCTTGTTTA TTAACTAAAG ATGTACAGCA     120

AACTGCCCGT TTAGAGTCCT CTTAATATTG ATGTCCTAAC ACTGGGTCTG CTTATGC        177

(2) INFORMATION FOR SEQ ID NO:24:

(i) SEQUENCE CHARACTERISTICS:
        (A) LENGTH: 167 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

GGCAGTGGGA TATGGAATCC AGAAGGGAAA CAAGCACTGG ATAATTAAAA ACAGCTGGGG      60

AGAAAACTGG GGAAACAAAG GATATATCCT CATGGCTCGA AATAAGAACA ACGCCTGTGG     120

CATTGCCAAC CTGGCCAGCT TCCCCAAGAT GTGACTCCAG CCAGAAA                   167

(2) INFORMATION FOR SEQ ID NO:25:

(i) SEQUENCE CHARACTERISTICS:
        (A) LENGTH: 151 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

GCCAGGGCGG ACCGTCTTTA TTCCTCTCCT GCCTCAGAGG TCAGGAAGGA GGTCTGGCAG      60

GACCTGCAGT GGGCCCTAGT CATCTGTGGC AGCGAAGGTG AAGGGACTCA CCTTGTCGCC    120

CGTGCCTGAG TAGAACTTGT TCTGGAATTC C                                   151

(2) INFORMATION FOR SEQ ID NO:26:

(i) SEQUENCE CHARACTERISTICS:
        (A) LENGTH: 156 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

AACTCTTTCA CACTCTGGTA TTTTTAGTTT AACAATATAT GTGTTGTGTC TTGGAAATTA      60

```
GTTCATATCA ATTCATATTG AGCTGTCTCA TTCTTTTTTT AATGGTCATA TACAGTAGTA    120

TTCAATTATA AGAATATATC CTAATACTTT TTAAAA                              156
```

(2) INFORMATION FOR SEQ ID NO:27:

(i) SEQUENCE CHARACTERISTICS:
        (A) LENGTH: 150 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

```
GGATAAGAAA GAAGGCCTGA GGGCTAGGGG CCGGGGCTGG CCTGCGTCTC AGTCCTGGGA     60

CGCAGCAGCC CGCACAGGTT GAGAGGGGCA CTTCCTCTTG CTTAGGTTGG TGAGGATCTG    120

GTCCTGGTTG GCCGGTGGAG AGCCACAAAA                                     150
```

(2) INFORMATION FOR SEQ ID NO:28:

(i) SEQUENCE CHARACTERISTICS:
        (A) LENGTH: 111 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

```
CTGACCTTCG AGAGTTTGAC CTGGAGCCGG ATACCTACTG CCGCTATGAC TCGGTCAGCG     60

TGTTCAACGG AGCCGTGAGC GACGACTCCG GTGGGAAGT TCTGCGGCGA T              111
```

(2) INFORMATION FOR SEQ ID NO:29:

(i) SEQUENCE CHARACTERISTICS:
        (A) LENGTH: 157 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

```
ATCCCTGGCT GTGGATAGTG CTTTTGTGTA GCAAATGCTC CCTCCTTAAG GTTATAGGGC     60

TCCCTGAGTT TGGGAGTGTG GAAGTACTAC TTAACTGTCT GTCCTGCTTG GCTGTCGTTA    120

TCGTTTTCTG GTGATGTTGT GCTAACAATA AGAATAC                             157
```

(2) INFORMATION FOR SEQ ID NO:30:

(i) SEQUENCE CHARACTERISTICS:
        (A) LENGTH: 152 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

```
GGCTGGGCAT CCCTCTCCTC CTCCATCCCC ATACATCACC AGGTCTAATG TTTACAAACG     60

GTGCCAGCCC GGCTCTGAAG CCAAGGGCCG TCCGTGCCAC GGTGGCTGTG AGTATTCCTC    120

CGTTAGCTTT CCCATAAGGT TGGAGTATCT GC                                  152
```

(2) INFORMATION FOR SEQ ID NO:31:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

```
CCAACTCCTA CCGCGATACA GACCCACAGA GTGCCATCCC TGAGAGACCA GACCGCTCCC        60

CAATACTCTC CTAAAATAAA CATGAAGCAC                                         90
```

(2) INFORMATION FOR SEQ ID NO:32:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

```
CATGGATGAA TGTCTCATGG TGGGAAGGAA CATGGTACAT TTC                          43
```

(2) INFORMATION FOR SEQ ID NO:33:

(i) SEQUENCE CHARACTERISTICS:
        (A) LENGTH: 2334 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

```
AGACACCTCT GCCCTCACCA TGAGCCTCTG GCAGCCCCTG GTCCTGGTGC TCCTGGTGCT        60

GGGCTGCTGC TTTGCTGCCC CCAGACAGCG CCAGTCCACC CTTGTGCTCT TCCCTGGAGA       120

CCTGAGAACC AATCTCACCG ACAGGCAGCT GGCAGAGGAA TACCTGTACC GCTATGGTTA       180

CACTCGGGTG GCAGAGATGC GTGGAGAGTC GAAATCTCTG GGGCCTGCGC TGCTGCTTCT       240

CCAGAAGCAA CTGTCCCTGC CGAGACCGG TGAGCTGGAT AGCGCCACGC TGAAGGCCAT        300

GCGAACCCCA CGGTGCGGGG TCCCAGACCT GGGCAGATTC CAAACCTTTG AGGGCGACCT       360

CAAGTGGCAC CACCACAACA TCACCTATTG GATCCAAAAC TACTCGGAAG ACTTGCCGCG       420

GGCGGTGATT GACGACGCCT TGCCCGCGC CTTCGCACTG TGGAGCGCGG TGACGCCGCT        480

CACCTTCACT CGCGTGTACA GCCGGGACGC AGACATCGTC ATCCAGTTTG GTGTCGCGGA       540

GCACGGAGAC GGGTATCCCT TCGACGGGAA GGACGGGCTC CTGGCACACG CCTTTCCTCC       600

TGGCCCCGGC ATTCAGGGAG ACGCCCATTT CGACGATGAC GAGTTGTGGT CCCTGGGCAA       660

GGGCGTCGTG GTTCCAACTC GGTTTGGAAA CGCAGATGGC GCGGCCTGCC ACTTCCCCTT       720

CATCTTCGAG GGCCGCTCCT ACTCTGCCTG CACCACCGAC GGTCGCTCCG ACGGGTTGCC       780

CTGGTGCAGT ACCACGGCCA ACTACGACAC CGACGACCGG TTTGGCTTCT GCCCCAGCGA       840

GAGACTCTAC ACCCGGGACG GCAATGCTGA TGGGAAACCC TGCCAGTTTC CATTCATCTT       900

CCAAGGCCAA TCCTACTCCG CCTGCACCAC GGACGGTCGC TCCGACGGCT ACCGCTGGTG       960

CGCCACCACC GCCAACTACG ACCGGGACAA GCTCTTCGGC TTCTGCCCGA CCCGAGCTGA      1020

CTCGACGGTG ATGGGGGGCA ACTCGGCGGG GGAGCTGTGC GTCTTCCCCT TCACTTTCCT      1080
```

```
GGGTAAGGAG TACTCGACCT GTACCAGCGA GGGCCGCGGA GATGGGCGCC TCTGGTGCGC      1140

TACCACCTCG AACTTTGACA GCGACAAGAA GTGGGGCTTC TGCCCGGACC AAGGATACAG      1200

TTTGTTCCTC GTGGCGGCGC ATGAGTTCGG CCACGCGCTG GGCTTAGATC ATTCCTCAGT      1260

GCCGGAGGCG CTCATGTACC CTATGTACCG CTTCACTGAG GGGCCCCCCT TGCATAAGGA      1320

CGACGTGAAT GGCATCCGGC ACCTCTATGG TCCTCGCCCT GAACCTGAGC CACGGCCTCC      1380

AACCACCACC ACACCGCAGC CCACGGCTCC CCCGACGGTC TGCCCCACCG GACCCCCCAC      1440

TGTCCACCCC TCAGAGCGCC CCACAGCTGG CCCCACAGGT CCCCCCTCAG CTGGCCCCAC      1500

AGGTCCCCCC ACTGCTGGCC CTTCTACGGC CACTACTGTG CCTTTGAGTC CGGTGGACGA      1560

TGCCTGCAAC GTGAACATCT TCGACGCCAT CGCGGAGATT GGGAACCAGC TGTATTTGTT      1620

CAAGGATGGG AAGTACTGGC GATTCTCTGA GGGCAGGGGG AGCCGGCCGC AGGGCCCCTT      1680

CCTTATCGCC GACAAGTGGC CCGCGCTGCC CCGCAAGCTG GACTCGGTCT TTGAGGAGCC      1740

GCTCTCCAAG AAGCTTTTCT TCTTCTCTGG GCGCCAGGTG TGGGTGTACA CAGGCGCGTC      1800

GGTGCTGGGC CCGAGGCGTC TGGACAAGCT GGGCCTGGGA GCCGACGTGG CCCAGGTGAC      1860

CGGGGCCCTC CGGAGTGGCA GGGGAAGAT GCTGCTGTTC AGCGGGCGGC GCCTCTGGAG      1920

GTTCGACGTG AAGGCGCAGA TGGTGGATCC CCGGAGCGCC AGCGAGGTGG ACCGGATGTT      1980

CCCCGGGGTG CCTTTGGACA CGCACGACGT CTTCCAGTAC CGAGAGAAAG CCTATTTCTG      2040

CCAGGACCGC TTCTACTGGC GCGTGAGTTC CCGGAGTGAG TTGAACCAGG TGGACCAAGT      2100

GGGCTACGTG ACCTATGACA TCCTGCAGTG CCCTGAGGAC TAGGGCTCCC GTCCTGCTTT      2160

GCAGTGCCAT GTAAATCCCC ACTGGGACCA ACCCTGGGGA AGGAGCCAGT TTGCCGGATA      2220

CAAACTGGTA TTCTGTTCTG GAGGAAAGGG AGGAGTGGAG GTGGGCTGGG CCCTCTCTTC      2280

TCACCTTTGT TTTTTGTTGG AGTGTTTCTA ATAAACTTGG ATTCTCTAAC CTTT           2334
```

(2) INFORMATION FOR SEQ ID NO:34:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:34:

```
Glu Ala Leu Met Tyr Pro Met Tyr Arg Phe Thr Glu Gly Pro Pro Leu
 1               5                  10                  15
His Lys
```

(2) INFORMATION FOR SEQ ID NO:35:

(i) SEQUENCE CHARACTERISTICS:
        (A) LENGTH: 1614 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 19..1005

(xi) SEQUENCE DESCRIPTION: SEQ ID NO:35:

```
CAGATTTCCA TCAGCAGG ATG TGG GGG CTC AAG GTT CTG CTG CTA CCT GTG       51
```

```
            Met Trp Gly Leu Lys Val Leu Leu Pro Val
             1               5                  10

GTG AGC TTT GCT CTG TAC CCT GAG GAG ATA CTG GAC ACC CAC TGG GAG        99
Val Ser Phe Ala Leu Tyr Pro Glu Glu Ile Leu Asp Thr His Trp Glu
             15                  20                  25

CTA TGG AAG AAG ACC CAC AGG AAG CAA TAT AAC AAC AAG GTG GAT GAA       147
Leu Trp Lys Lys Thr His Arg Lys Gln Tyr Asn Asn Lys Val Asp Glu
         30                  35                  40

ATC TCT CCC CGT TTA ATT TGG GAA AAA AAC CTG AAG TAT ATT TCC ATC       195
Ile Ser Pro Arg Leu Ile Trp Glu Lys Asn Leu Lys Tyr Ile Ser Ile
         45                  50                  55

CAT AAC CTT GAG GCT TCT CTT GGT GTC CAT ACA TAT GAA CTG GCT ATG       243
His Asn Leu Glu Ala Ser Leu Gly Val His Thr Tyr Glu Leu Ala Met
 60                  65                  70                  75

AAC CAC CTG GGG GAC ATG ACC AGT GAA GAG GTG GTT CAG AAG ATG ACT       291
Asn His Leu Gly Asp Met Thr Ser Glu Glu Val Val Gln Lys Met Thr
                 80                  85                  90

GGA CTC AAA GTA CCC CTG TCT CAT TCC CGC AGT AAT GAC ACC CTT TAT       339
Gly Leu Lys Val Pro Leu Ser His Ser Arg Ser Asn Asp Thr Leu Tyr
             95                 100                 105

ATC CCA GAA TGG GAA GGT AGA GCC CCA GAC TCT GTC GAC TAT CGA AAG       387
Ile Pro Glu Trp Glu Gly Arg Ala Pro Asp Ser Val Asp Tyr Arg Lys
             110                 115                 120

AAA GGA TAT GTT ACT CCT GTC AAA AAT CAG GGT CAG TGT GGT TCC TGT       435
Lys Gly Tyr Val Thr Pro Val Lys Asn Gln Gly Gln Cys Gly Ser Cys
         125                 130                 135

TGG GCT TTT AGC TCT GTG GGT GCC CTG GAG GGC CAA CTC AAG AAG AAA       483
Trp Ala Phe Ser Ser Val Gly Ala Leu Glu Gly Gln Leu Lys Lys Lys
140                 145                 150                 155

ACT GGC AAA CTC TTA AAT CTG AGT CCC CAG AAC CTA GTG GAT TGT GTG       531
Thr Gly Lys Leu Leu Asn Leu Ser Pro Gln Asn Leu Val Asp Cys Val
                 160                 165                 170

TCT GAG AAT GAT GGC TGT GGA GGG GGC TAC ATG ACC AAT GCC TTC CAA       579
Ser Glu Asn Asp Gly Cys Gly Gly Gly Tyr Met Thr Asn Ala Phe Gln
             175                 180                 185

TAT GTG CAG AAG AAC CGG GGT ATT GAC TCT GAA GAT GCC TAC CCA TAT       627
Tyr Val Gln Lys Asn Arg Gly Ile Asp Ser Glu Asp Ala Tyr Pro Tyr
             190                 195                 200

GTG GGA CAG GAA GAG AGT TGT ATG TAC AAC CCA ACA GGC AAG GCA GCT       675
Val Gly Gln Glu Glu Ser Cys Met Tyr Asn Pro Thr Gly Lys Ala Ala
         205                 210                 215

AAA TGC AGA GGG TAC AGA GAG ATC CCC GAG GGG AAT GAG AAA GCC CTG       723
Lys Cys Arg Gly Tyr Arg Glu Ile Pro Glu Gly Asn Glu Lys Ala Leu
220                 225                 230                 235

AAG AGG GCA GTG GCC CGA GTG GGA CCT GTC TCT GTG GCC ATT GAT GCA       771
Lys Arg Ala Val Ala Arg Val Gly Pro Val Ser Val Ala Ile Asp Ala
                 240                 245                 250

AGC CTG ACC TCC TTC CAG TTT TAC AGC AAA GGT GTG TAT TAT GAT GAA       819
Ser Leu Thr Ser Phe Gln Phe Tyr Ser Lys Gly Val Tyr Tyr Asp Glu
             255                 260                 265

AGC TGC AAT AGC GAT AAT CTG AAC CAT GCG GTT TTG GCA GTG GGA TAT       867
Ser Cys Asn Ser Asp Asn Leu Asn His Ala Val Leu Ala Val Gly Tyr
             270                 275                 280

GGA ATC CAG AAG GGA AAC AAG CAC TGG ATA ATT AAA AAC AGC TGG GGA       915
Gly Ile Gln Lys Gly Asn Lys His Trp Ile Ile Lys Asn Ser Trp Gly
         285                 290                 295

GAA AAC TGG GGA AAC AAA GGA TAT ATC CTC ATG GCT CGA AAT AAG AAC       963
Glu Asn Trp Gly Asn Lys Gly Tyr Ile Leu Met Ala Arg Asn Lys Asn
300                 305                 310                 315
```

```
AAC GCC TGT GGC ATT GCC AAC CTG GCC AGC TTC CCC AAG ATG         1005
Asn Ala Cys Gly Ile Ala Asn Leu Ala Ser Phe Pro Lys Met
                320                 325

TGACTCCAGC CAGCCAAATC CATCCTGCTC TTCCATTTCT TCCACGATGG TGCAGTGTAA  1065

CGATGCACTT TGGAAGGGAG TTGGTGTGCT ATTTTTGAAG CAGATGTGGT GATACTGAGA  1125

TTGTCTGTTC AGTTTCCCCA TTTGTTTGTG CTTCAAATGA TCCTTCCTAC TTTCGTTCTC  1185

TCCACCCATG ACCTTTTTCA CTGTGGCGAT CAGGACTTTC CCTGACAGCT GTGTACTCTT  1245

AGGCTAAGAG ATGTGACTAC AGCCTGCCCC TGACTGTGTT GTCCCAGGGC TGATGCTGTA  1305

CAGGTACAGG CTGGAGATTT TCACATAGGT TAGATTCTCA TTCACGGGAC TAGTTAGCTT  1365

TAAGCACCCT AGAGGACTAG GGTAATCTGA CTTCCTAAGT TCCCTTCTAT ATCCTCAAGG  1425

TAGAAATGTC TATGTTTTCT ACTCCAATTC ATAAATCTAT TCATAAGTCT TTGGTACAAG  1485

TTTACATGAT AAAAGAAAT GTGATTTGTC TTCCCTTCTT TGCACTTTTG AAATAAAGTA   1545

TTTATCTCCT GTCTACAGTT AATAAATAG CATCTAGTAC ACATCACATT CAAAAAAAA   1605

AAAAAAAA                                                          1614

(2) INFORMATION FOR SEQ ID NO:36:

(i) SEQUENCE CHARACTERISTICS:
        (A) LENGTH: 329 amino acids
        (B) TYPE: amino acid
        (D) TOPOLOGY: linear (ii) MOLECULE TYPE: protein (xi) SEQUENCE DESCRIPTION: SEQ ID NO:36:

Met Trp Gly Leu Lys Val Leu Leu Pro Val Ser Phe Ala Leu
 1               5                  10                  15

Tyr Pro Glu Glu Ile Leu Asp Thr His Trp Glu Leu Trp Lys Lys Thr
                20                  25                  30

His Arg Lys Gln Tyr Asn Asn Lys Val Asp Glu Ile Ser Pro Arg Leu
            35                  40                  45

Ile Trp Glu Lys Asn Leu Lys Tyr Ile Ser Ile His Asn Leu Glu Ala
    50                  55                  60

Ser Leu Gly Val His Thr Tyr Glu Leu Ala Met Asn His Leu Gly Asp
65                  70                  75                  80

Met Thr Ser Glu Glu Val Val Gln Lys Met Thr Gly Leu Lys Val Pro
                85                  90                  95

Leu Ser His Ser Arg Ser Asn Asp Thr Leu Tyr Ile Pro Glu Trp Glu
            100                 105                 110

Gly Arg Ala Pro Asp Ser Val Asp Tyr Arg Lys Gly Tyr Val Thr
        115                 120                 125

Pro Val Lys Asn Gln Gly Gln Cys Gly Ser Cys Trp Ala Phe Ser Ser
130                 135                 140

Val Gly Ala Leu Glu Gly Gln Leu Lys Lys Thr Gly Lys Leu Leu
145                 150                 155                 160

Asn Leu Ser Pro Gln Asn Leu Val Asp Cys Val Ser Glu Asn Asp Gly
                165                 170                 175

Cys Gly Gly Gly Tyr Met Thr Asn Ala Phe Gln Tyr Val Gln Lys Asn
            180                 185                 190

Arg Gly Ile Asp Ser Glu Asp Ala Tyr Pro Tyr Val Gly Gln Glu Glu
        195                 200                 205

Ser Cys Met Tyr Asn Pro Thr Gly Lys Ala Ala Lys Cys Arg Gly Tyr
210                 215                 220
```

```
Arg Glu Ile Pro Glu Gly Asn Glu Lys Ala Leu Lys Arg Ala Val Ala
225                 230                 235                 240

Arg Val Gly Pro Val Ser Val Ala Ile Asp Ala Ser Leu Thr Ser Phe
            245                 250                 255

Gln Phe Tyr Ser Lys Gly Val Tyr Tyr Asp Glu Ser Cys Asn Ser Asp
        260                 265                 270

Asn Leu Asn His Ala Val Leu Ala Val Gly Tyr Gly Ile Gln Lys Gly
    275                 280                 285

Asn Lys His Trp Ile Ile Lys Asn Ser Trp Gly Glu Asn Trp Gly Asn
290                 295                 300

Lys Gly Tyr Ile Leu Met Ala Arg Asn Lys Asn Asn Ala Cys Gly Ile
305                 310                 315                 320

Ala Asn Leu Ala Ser Phe Pro Lys Met
            325
```

(2) INFORMATION FOR SEQ ID NO:37:

(i) SEQUENCE CHARACTERISTICS:
        (A) LENGTH: 2640 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 58..2523

(xi) SEQUENCE DESCRIPTION: SEQ ID NO:37:

```
CGGCGTGCGC GGACGGGCAG CCAGCAGCGG AGGCGCGGCG CAGCACACCC GGGGACC            57

ATG GGC TCC ATG TTC CGG AGC GAG GAG GTG GCC CTG GTC CAG CTC TTT         105
Met Gly Ser Met Phe Arg Ser Glu Glu Val Ala Leu Val Gln Leu Phe
 1               5                  10                  15

CTG CCC ACA GCG GCT GCC TAC ACC TGC GTG AGT CGG CTG GGC GAG CTG         153
Leu Pro Thr Ala Ala Ala Tyr Thr Cys Val Ser Arg Leu Gly Glu Leu
            20                  25                  30

GGC CTC GTG GAG TTC AGA GAC CTC AAC GCC TCG GTG AGC GCC TTC CAG         201
Gly Leu Val Glu Phe Arg Asp Leu Asn Ala Ser Val Ser Ala Phe Gln
        35                  40                  45

AGA CGC TTT GTG GTT GAT GTT TGG CGC TGT GAG GAG CTG GAG AAG ACC         249
Arg Arg Phe Val Val Asp Val Trp Arg Cys Glu Glu Leu Glu Lys Thr
    50                  55                  60

TTC ACC TTC CTG CAG GAG GAG GTG CGG CGG GCT GGG CTG GTC CTG CCC         297
Phe Thr Phe Leu Gln Glu Glu Val Arg Arg Ala Gly Leu Val Leu Pro
65                  70                  75                  80

CCG CCA AAG GGG AGG CTG CCG GCA CCC CCA CCC CGG GAC CTG CTG CGC         345
Pro Pro Lys Gly Arg Leu Pro Ala Pro Pro Pro Arg Asp Leu Leu Arg
                85                  90                  95

ATC CAG GAG GAG ACG GAG CGC CTG GCC CAG GAG CTG CGG GAT GTG CGG         393
Ile Gln Glu Glu Thr Glu Arg Leu Ala Gln Glu Leu Arg Asp Val Arg
            100                 105                 110

GGC AAC CAG CAG GCC CTG CGG GCC CAG CTG CAC CAG CTG CAG CTC CAC         441
Gly Asn Gln Gln Ala Leu Arg Ala Gln Leu His Gln Leu Gln Leu His
        115                 120                 125

GCC GCC GTG CTA CGC CAG GGC CAT GAA CCT CAG CTG GCA GCC GCC CAC         489
Ala Ala Val Leu Arg Gln Gly His Glu Pro Gln Leu Ala Ala Ala His
    130                 135                 140

ACA GAT GGG GCC TCA GAG AGG ACG CCC CTG CTC CAG GCC CCC GGG GGG         537
Thr Asp Gly Ala Ser Glu Arg Thr Pro Leu Leu Gln Ala Pro Gly Gly
```

-continued

```
        145                 150                 155                 160
CCG CAC CAG GAC CTG AGG GTC AAC TTT GTG GCA GGT GCC GTG GAG CCC         585
Pro His Gln Asp Leu Arg Val Asn Phe Val Ala Gly Ala Val Glu Pro
                    165                 170                 175

CAC AAG GCC CCT GCC CTA GAG CGC CTG CTC TGG AGG GCC TGC CGC GGC         633
His Lys Ala Pro Ala Leu Glu Arg Leu Leu Trp Arg Ala Cys Arg Gly
                180                 185                 190

TTC CTC ATT GCC AGC TTC AGG GAG CTG GAG CAG CCG CTG GAG CAC CCC         681
Phe Leu Ile Ala Ser Phe Arg Glu Leu Glu Gln Pro Leu Glu His Pro
                195                 200                 205

GTG ACG GGC GAG CCA GCC ACG TGG ATG ACC TTC CTC ATC TCC TAC TGG         729
Val Thr Gly Glu Pro Ala Thr Trp Met Thr Phe Leu Ile Ser Tyr Trp
            210                 215                 220

GGT GAG CAG ATC GGA CAG AAG ATC CGC AAG ATC ACG GAC TGC TTC CAC         777
Gly Glu Gln Ile Gly Gln Lys Ile Arg Lys Ile Thr Asp Cys Phe His
225                 230                 235                 240

TGC CAC GTC TTC CCG TTT CTG CAG CAG GAG GAG GCC CGC CTC GGG GCC         825
Cys His Val Phe Pro Phe Leu Gln Gln Glu Glu Ala Arg Leu Gly Ala
                245                 250                 255

CTG CAG CAG CTG CAA CAG CAG AGC CAG GAG CTG CAG GAG GTC CTC GGG         873
Leu Gln Gln Leu Gln Gln Gln Ser Gln Glu Leu Gln Glu Val Leu Gly
                260                 265                 270

GAG ACA GAG CGG TTC CTG AGC CAG GTG CTA GGC CGG GTG CTG CAG CTG         921
Glu Thr Glu Arg Phe Leu Ser Gln Val Leu Gly Arg Val Leu Gln Leu
            275                 280                 285

CTG CCG CCA GGG CAG GTG CAG GTC CAC AAG ATG AAG GCC GTG TAC CTG         969
Leu Pro Pro Gly Gln Val Gln Val His Lys Met Lys Ala Val Tyr Leu
290                 295                 300

GCC CTG AAC CAG TGC AGC GTG AGC ACC ACG CAC AAG TGC CTC ATT GCC        1017
Ala Leu Asn Gln Cys Ser Val Ser Thr Thr His Lys Cys Leu Ile Ala
305                 310                 315                 320

GAG GCC TGG TGC TCT GTG CGA GAC CTG CCC GCC CTG CAG GAG GCC CTG        1065
Glu Ala Trp Cys Ser Val Arg Asp Leu Pro Ala Leu Gln Glu Ala Leu
                325                 330                 335

CGG GAC AGC TCG ATG GAG GAG GGA GTG AGT GCC GTG GCT CAC CGC ATC        1113
Arg Asp Ser Ser Met Glu Glu Gly Val Ser Ala Val Ala His Arg Ile
                340                 345                 350

CCC TGC CGG GAC ATG CCC CCC ACA CTC ATC CGC ACC AAC CGC TTC ACG        1161
Pro Cys Arg Asp Met Pro Pro Thr Leu Ile Arg Thr Asn Arg Phe Thr
            355                 360                 365

GCC AGC TTC CAG GGC ATC GTG GAT CGC TAC GGC GTG GGC CGC TAC CAG        1209
Ala Ser Phe Gln Gly Ile Val Asp Arg Tyr Gly Val Gly Arg Tyr Gln
            370                 375                 380

GAG GTC AAC CCC GCT CCC TAC ACC ATC ATC ACC TTC CCC TTC CTG TTT        1257
Glu Val Asn Pro Ala Pro Tyr Thr Ile Ile Thr Phe Pro Phe Leu Phe
385                 390                 395                 400

GCT GTG ATG TTC GGG GAT GTG GGC CAC GGG CTG CTC ATG TTC CTC TTC        1305
Ala Val Met Phe Gly Asp Val Gly His Gly Leu Leu Met Phe Leu Phe
                405                 410                 415

GCC CTG GCC ATG GTC CTT GCG GAG AAC CGA CCG GCT GTG AAA GCC GCG        1353
Ala Leu Ala Met Val Leu Ala Glu Asn Arg Pro Ala Val Lys Ala Ala
                420                 425                 430

CAG AAC GAG ATC TGG CAG ACT TTC TTC AGG GGC CGC TAC CTG CTC CTG        1401
Gln Asn Glu Ile Trp Gln Thr Phe Phe Arg Gly Arg Tyr Leu Leu Leu
                435                 440                 445

CTT ATG GGC CTG TTC TCC ATC TAC ACC GGC TTC ATC TAC AAC GAG TGC        1449
Leu Met Gly Leu Phe Ser Ile Tyr Thr Gly Phe Ile Tyr Asn Glu Cys
            450                 455                 460

TTC AGT CGC GCC ACC AGC ATC TTC CCC TCG GGC TGG AGT GTG GCC GCC        1497
```

```
Phe Ser Arg Ala Thr Ser Ile Phe Pro Ser Gly Trp Ser Val Ala Ala
465                 470                 475                 480

ATG GCC AAC CAG TCT GGC TGG AGT GAT GCA TTC CTG GCC CAG CAC ACG        1545
Met Ala Asn Gln Ser Gly Trp Ser Asp Ala Phe Leu Ala Gln His Thr
                485                 490                 495

ATG CTT ACC CTG GAT CCC AAC GTC ACC GGT GTC TTC CTG GGA CCC TAC        1593
Met Leu Thr Leu Asp Pro Asn Val Thr Gly Val Phe Leu Gly Pro Tyr
            500                 505                 510

CCC TTT GGC ATC GAT CCT ATT TGG AGC CTG GCT GCC AAC CAC TTG AGC        1641
Pro Phe Gly Ile Asp Pro Ile Trp Ser Leu Ala Ala Asn His Leu Ser
                515                 520                 525

TTC CTC AAC TCC TTC AAG ATG AAG ATG TCC GTC ATC CTG GGC GTC GTG        1689
Phe Leu Asn Ser Phe Lys Met Lys Met Ser Val Ile Leu Gly Val Val
530                 535                 540

CAC ATG GCC TTT GGG GTG GTC CTC GGA GTC TTC AAC CAC GTG CAC TTT        1737
His Met Ala Phe Gly Val Val Leu Gly Val Phe Asn His Val His Phe
545                 550                 555                 560

GGC CAG AGG CAC CGG CTG CTG CTG GAG ACG CTG CCG GAG CTC ACC TTC        1785
Gly Gln Arg His Arg Leu Leu Leu Glu Thr Leu Pro Glu Leu Thr Phe
                565                 570                 575

CTG CTG GGA CTC TTC GGT TAC CTC GTG TTC CTA GTC ATC TAC AAG TGG        1833
Leu Leu Gly Leu Phe Gly Tyr Leu Val Phe Leu Val Ile Tyr Lys Trp
            580                 585                 590

CTG TGT GTC TGG GCT GCC AGG GCC GCC TCG CCC AGC ATC CTC ATC CAC        1881
Leu Cys Val Trp Ala Ala Arg Ala Ala Ser Pro Ser Ile Leu Ile His
                595                 600                 605

TTC ATC AAC ATG TTC CTC TTC TCC CAC AGC CCC AGC AAC AGG CTG CTC        1929
Phe Ile Asn Met Phe Leu Phe Ser His Ser Pro Ser Asn Arg Leu Leu
610                 615                 620

TAC CCC CGG CAG GAG GTG GTC CAG GCC ACG CTG GTG GTC CTG GCC TTG        1977
Tyr Pro Arg Gln Glu Val Val Gln Ala Thr Leu Val Val Leu Ala Leu
625                 630                 635                 640

GCC ATG GTG CCC ATC CTG CTG CTT GGC ACA CCC CTG CAC CTG CTG CAC        2025
Ala Met Val Pro Ile Leu Leu Leu Gly Thr Pro Leu His Leu Leu His
                645                 650                 655

CGC CAC CGC CGC CGC CTG CGG AGG AGG CCC GCT GAC CGA CAG GAG GAA        2073
Arg His Arg Arg Arg Leu Arg Arg Arg Pro Ala Asp Arg Gln Glu Glu
                660                 665                 670

AAC AAG GCC GGG TTG CTG GAC CTG CCT GAC GCA TCT GTG AAT GGC TGG        2121
Asn Lys Ala Gly Leu Leu Asp Leu Pro Asp Ala Ser Val Asn Gly Trp
            675                 680                 685

AGC TCC GAT GAG GAA AAG GCA GGG GGC CTG GAT GAT GAA GAG GAG GCC        2169
Ser Ser Asp Glu Glu Lys Ala Gly Gly Leu Asp Asp Glu Glu Glu Ala
690                 695                 700

GAG CTC GTC CCC TCC GAG GTG CTC ATG CAC CAG GCC ATC CAC ACC ATC        2217
Glu Leu Val Pro Ser Glu Val Leu Met His Gln Ala Ile His Thr Ile
705                 710                 715                 720

GAG TTC TGC CTG GGC TGC GTC TCC AAC ACC GCC TCC TAC CTG CGC CTG        2265
Glu Phe Cys Leu Gly Cys Val Ser Asn Thr Ala Ser Tyr Leu Arg Leu
                725                 730                 735

TGG GCC CTG AGC CTG GCC CAC GCC CAG CTG TCC GAG GTT CTG TGG GCC        2313
Trp Ala Leu Ser Leu Ala His Ala Gln Leu Ser Glu Val Leu Trp Ala
                740                 745                 750

ATG GTG ATG CGC ATA GGC CTG GGC CTG GGC CGG GAG GTG GGC GTG GCG        2361
Met Val Met Arg Ile Gly Leu Gly Leu Gly Arg Glu Val Gly Val Ala
            755                 760                 765

GCT GTG GTG CTG GTC CCC ATC TTT GCC GCC TTT GCC GTG ATG ACC GTG        2409
Ala Val Val Leu Val Pro Ile Phe Ala Ala Phe Ala Val Met Thr Val
                770                 775                 780
```

```
GCT ATC CTG CTG GTG ATG GAG GGA CTC TCA GCC TTC CTG CAC GCC CTG       2457
Ala Ile Leu Leu Val Met Glu Gly Leu Ser Ala Phe Leu His Ala Leu
785                 790                 795                 800

CGG CTG CAC TGG GTG GAA TTC CAG AAC AAG TTC TAC TCA GGC ACG GGC       2505
Arg Leu His Trp Val Glu Phe Gln Asn Lys Phe Tyr Ser Gly Thr Gly
                805                 810                 815

TAC AAG CTG AGT CCC TTC ACCTTCGCTG CCACAGATGA CTAGGGCCCA              2553
Tyr Lys Leu Ser Pro Phe
                820

CTGCAGGTCC TGCCAGACCT CCTTCCTGAC CTCTGAGGCA GGAGAGGAAT AAAGACGGTC     2613

CGCCCTGGCA AAAAAAAAAA AAAAAA                                          2640
```

(2) INFORMATION FOR SEQ ID NO:38:

(i) SEQUENCE CHARACTERISTICS:
        (A) LENGTH: 822 amino acids
        (B) TYPE: amino acid
        (D) TOPOLOGY: linear (ii) MOLECULE TYPE: protein (xi) SEQUENCE DESCRIPTION: SEQ ID NO:38:

```
Met Gly Ser Met Phe Arg Ser Glu Glu Val Ala Leu Val Gln Leu Phe
1               5                   10                  15

Leu Pro Thr Ala Ala Tyr Thr Cys Val Ser Arg Leu Gly Glu Leu
            20                  25                  30

Gly Leu Val Glu Phe Arg Asp Leu Asn Ala Ser Val Ser Ala Phe Gln
            35                  40                  45

Arg Arg Phe Val Val Asp Val Trp Arg Cys Glu Glu Leu Glu Lys Thr
        50                  55                  60

Phe Thr Phe Leu Gln Glu Val Arg Ala Gly Leu Val Leu Pro
65                  70                  75                  80

Pro Pro Lys Gly Arg Leu Pro Ala Pro Pro Arg Asp Leu Leu Arg
                85                  90                  95

Ile Gln Glu Glu Thr Glu Arg Leu Ala Gln Glu Leu Arg Asp Val Arg
            100                 105                 110

Gly Asn Gln Gln Ala Leu Arg Ala Gln Leu His Gln Leu Gln Leu His
            115                 120                 125

Ala Ala Val Leu Arg Gln Gly His Glu Pro Gln Leu Ala Ala His
130                 135                 140

Thr Asp Gly Ala Ser Glu Arg Thr Pro Leu Leu Gln Ala Pro Gly Gly
145                 150                 155                 160

Pro His Gln Asp Leu Arg Val Asn Phe Val Ala Gly Ala Val Glu Pro
                165                 170                 175

His Lys Ala Pro Ala Leu Glu Arg Leu Leu Trp Arg Ala Cys Arg Gly
            180                 185                 190

Phe Leu Ile Ala Ser Phe Arg Glu Leu Glu Gln Pro Leu Glu His Pro
            195                 200                 205

Val Thr Gly Glu Pro Ala Thr Trp Met Thr Phe Leu Ile Ser Tyr Trp
        210                 215                 220

Gly Glu Gln Ile Gly Gln Lys Ile Arg Lys Ile Thr Asp Cys Phe His
225                 230                 235                 240

Cys His Val Phe Pro Phe Leu Gln Gln Glu Ala Arg Leu Gly Ala
                245                 250                 255

Leu Gln Gln Leu Gln Gln Ser Gln Glu Leu Gln Glu Val Leu Gly
            260                 265                 270
```

-continued

Glu Thr Glu Arg Phe Leu Ser Gln Val Leu Gly Arg Val Leu Gln Leu
            275                 280                 285

Leu Pro Pro Gly Gln Val Gln Val His Lys Met Lys Ala Val Tyr Leu
        290                 295                 300

Ala Leu Asn Gln Cys Ser Val Ser Thr Thr His Lys Cys Leu Ile Ala
305                 310                 315                 320

Glu Ala Trp Cys Ser Val Arg Asp Leu Pro Ala Leu Gln Glu Ala Leu
                325                 330                 335

Arg Asp Ser Ser Met Glu Glu Gly Val Ser Ala Val Ala His Arg Ile
            340                 345                 350

Pro Cys Arg Asp Met Pro Pro Thr Leu Ile Arg Thr Asn Arg Phe Thr
        355                 360                 365

Ala Ser Phe Gln Gly Ile Val Asp Arg Tyr Gly Val Gly Arg Tyr Gln
370                 375                 380

Glu Val Asn Pro Ala Pro Tyr Thr Ile Ile Thr Phe Pro Phe Leu Phe
385                 390                 395                 400

Ala Val Met Phe Gly Asp Val Gly His Gly Leu Leu Met Phe Leu Phe
                405                 410                 415

Ala Leu Ala Met Val Leu Ala Glu Asn Arg Pro Ala Val Lys Ala Ala
            420                 425                 430

Gln Asn Glu Ile Trp Gln Thr Phe Phe Arg Gly Arg Tyr Leu Leu Leu
        435                 440                 445

Leu Met Gly Leu Phe Ser Ile Tyr Thr Gly Phe Ile Tyr Asn Glu Cys
450                 455                 460

Phe Ser Arg Ala Thr Ser Ile Phe Pro Ser Gly Trp Ser Val Ala Ala
465                 470                 475                 480

Met Ala Asn Gln Ser Gly Trp Ser Asp Ala Phe Leu Ala Gln His Thr
                485                 490                 495

Met Leu Thr Leu Asp Pro Asn Val Thr Gly Val Phe Leu Gly Pro Tyr
            500                 505                 510

Pro Phe Gly Ile Asp Pro Ile Trp Ser Leu Ala Ala Asn His Leu Ser
        515                 520                 525

Phe Leu Asn Ser Phe Lys Met Lys Met Ser Val Ile Leu Gly Val Val
530                 535                 540

His Met Ala Phe Gly Val Val Leu Gly Val Phe Asn His Val His Phe
545                 550                 555                 560

Gly Gln Arg His Arg Leu Leu Leu Glu Thr Leu Pro Glu Leu Thr Phe
                565                 570                 575

Leu Leu Gly Leu Phe Gly Tyr Leu Val Phe Leu Val Ile Tyr Lys Trp
            580                 585                 590

Leu Cys Val Trp Ala Ala Arg Ala Ala Ser Pro Ser Ile Leu Ile His
        595                 600                 605

Phe Ile Asn Met Phe Leu Phe Ser His Ser Pro Ser Asn Arg Leu Leu
610                 615                 620

Tyr Pro Arg Gln Glu Val Val Gln Ala Thr Leu Val Val Leu Ala Leu
625                 630                 635                 640

Ala Met Val Pro Ile Leu Leu Leu Gly Thr Pro Leu His Leu Leu His
                645                 650                 655

Arg His Arg Arg Arg Leu Arg Arg Pro Ala Asp Arg Gln Glu Glu
            660                 665                 670

Asn Lys Ala Gly Leu Leu Asp Leu Pro Asp Ala Ser Val Asn Gly Trp
        675                 680                 685

Ser Ser Asp Glu Glu Lys Ala Gly Gly Leu Asp Asp Glu Glu Glu Ala

```
                        690                 695                 700
Glu Leu Val Pro Ser Glu Val Leu Met His Gln Ala Ile His Thr Ile
705                     710                 715                 720

Glu Phe Cys Leu Gly Cys Val Ser Asn Thr Ala Ser Tyr Leu Arg Leu
                    725                 730                 735

Trp Ala Leu Ser Leu Ala His Ala Gln Leu Ser Glu Val Leu Trp Ala
                740                 745                 750

Met Val Met Arg Ile Gly Leu Gly Leu Gly Arg Glu Val Gly Val Ala
            755                 760                 765

Ala Val Val Leu Val Pro Ile Phe Ala Ala Phe Ala Val Met Thr Val
        770                 775                 780

Ala Ile Leu Leu Val Met Glu Gly Leu Ser Ala Phe Leu His Ala Leu
785                 790                 795                 800

Arg Leu His Trp Val Glu Phe Gln Asn Lys Phe Tyr Ser Gly Thr Gly
                805                 810                 815

Tyr Lys Leu Ser Pro Phe
                820
```